United States Patent
Elcombe et al.

(10) Patent No.: US 8,487,003 B2
(45) Date of Patent: Jul. 16, 2013

(54) TREATMENT OF CANCER BY ADMINISTRATION OF PERFLUOROOCTANOIC ACID

(75) Inventors: Clifford R. Elcombe, Meigle (GB); Charles R. Wolf, Inchture (GB)

(73) Assignee: CXR Biosciences Limited, Dundee (GB)

(*) Notice: Subject to any disclaimer, the term of this patent is extended or adjusted under 35 U.S.C. 154(b) by 1676 days.

(21) Appl. No.: 10/468,331

(22) PCT Filed: Feb. 18, 2002

(86) PCT No.: PCT/GB02/00726
§ 371 (c)(1),
(2), (4) Date: Jan. 27, 2004

(87) PCT Pub. No.: WO02/066028
PCT Pub. Date: Aug. 29, 2002

(65) Prior Publication Data
US 2005/0175639 A1    Aug. 11, 2005

(30) Foreign Application Priority Data
Feb. 16, 2001    (GB) .................................. 0103809.0

(51) Int. Cl.
*A01N 37/00*    (2006.01)
*A61K 31/20*    (2006.01)

(52) U.S. Cl.
USPC ........................................................ 514/558

(58) Field of Classification Search
None
See application file for complete search history.

(56) References Cited

U.S. PATENT DOCUMENTS

| 2,567,011 A | 9/1951 | Diesslin et al. |
| 4,624,851 A | 11/1986 | Revici |
| 5,621,144 A | 4/1997 | Cooper |
| 6,013,795 A | 1/2000 | Manzara et al. |
| 6,015,838 A | 1/2000 | Stern et al. |
| 6,028,109 A * | 2/2000 | Willson ........................ 514/567 |
| 2004/0077220 A1 | 4/2004 | Musolf et al. |

FOREIGN PATENT DOCUMENTS

| WO | WO 92/11248 | 7/1992 |
| WO | WO 00/06143 | 2/2000 |
| WO | WO 01/07066 | 2/2001 |
| WO | WO 2004/019927 A2 | 3/2004 |

OTHER PUBLICATIONS

Intrasuskri et al.,Mechanisms of Peroxisome Proliferation by Perfluorooctanoic Acid and Endogenous Fatty Acid, General Pharmacology, vol. 31, No. 2. pp. 187-197, 1998.*
Merriam-Webster's Collegiate Dictionary, 1996, Tenth Edition, 3 Page.*

(Continued)

*Primary Examiner* — James H Alstrum Acevedo
*Assistant Examiner* — Thor Nielsen
(74) *Attorney, Agent, or Firm* — Ryan Kromholz & Manion, S.C.

(57) ABSTRACT

The molecules of formula (I) are useful in treating diabetes, obesity, hypercholesterolaemia, hyperlipidaemia, cancer, inflammation or other conditions in which modulation of lipid or eicosanoid status or functions may be desirable. Formula (I): $Z^1$—X—$Z^2$ wherein a) $Z^1$ represents $CO_2H$ or a derivative thereof; b) $Z^2$ represents F, H, —$CO_2H$ or a derivative thereof; and c) X represents fluorinated alkylene; or a solvate thereof, for example a perfluorinated fatty acid or derivative thereof.

4 Claims, 38 Drawing Sheets

OTHER PUBLICATIONS

Figure 1:
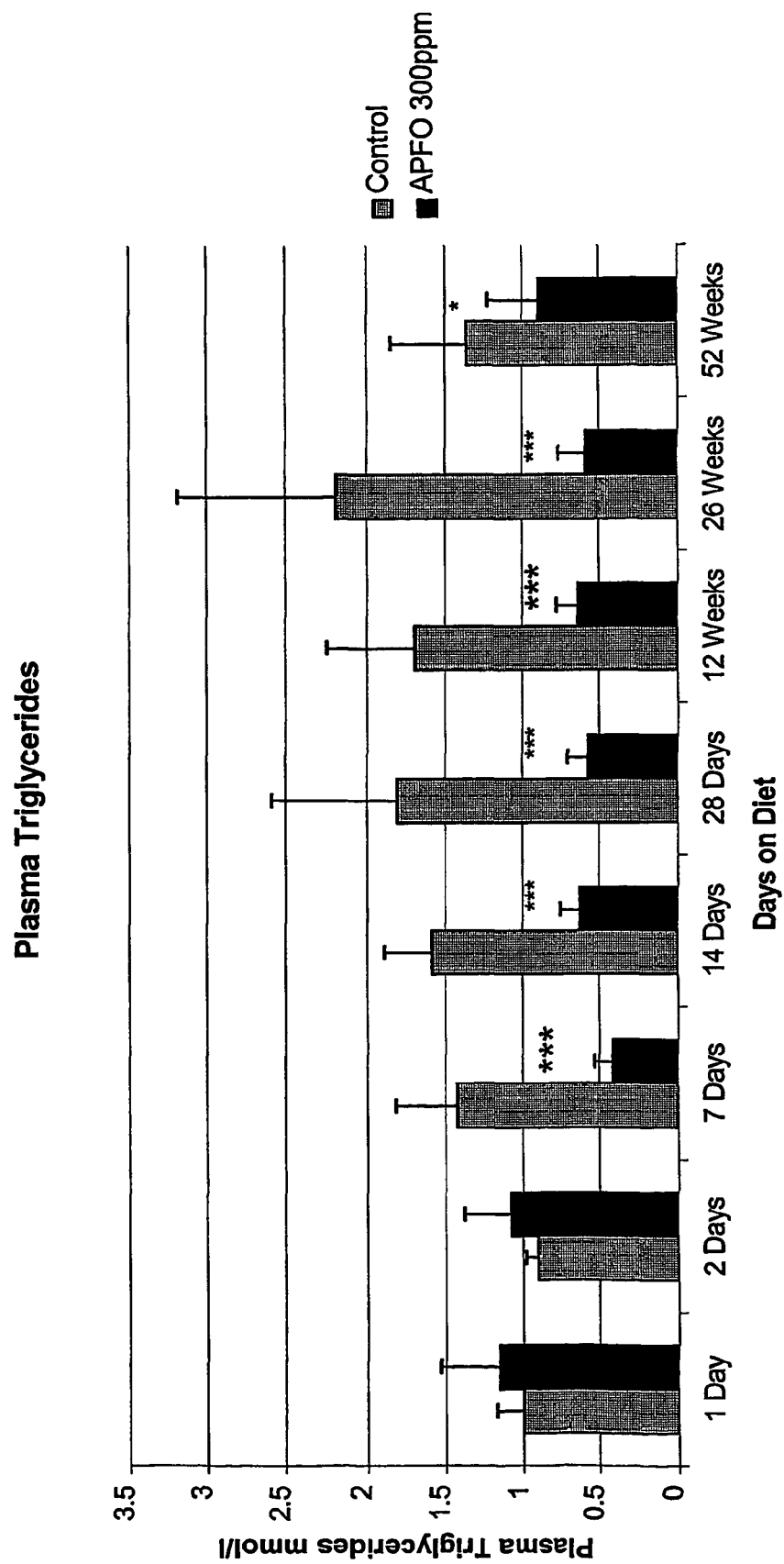

Abstract, Vredenburgh JJ, Experience with irinotecan for the treatment of malignant glioma, Neuro-Oncology, 11(1):80-91, 2009.*
El-Rayes et al., Hormonal therapy for prostate cancer: past, present and future, Experimental Review in Anticancer Therapy, 2(1), 37-47 (2002).*
Draft Risk Assessment of Potential Human health Effects associated with exposure to PFOA, EPA. 2005.*
Perfluoroalkyl Acids, Breast Cancer and The Environment Research Center Fact Sheet, 2007.*
Poondru, Lack of in Vitro—in Vivo Correlation of a Novel Investigational Anticancer Agent, SH 30, Investigational New Drugs, abstract.*
Perfluorinated compounds, Pollution in People, <http://www.pollutioninpeople.org/toxics/pfcs>.*
El-Reyes et al., Hormonal therapy for prostate cancer: past, present and future, Experimental Review in Anticancer Therapy, :>(1), 37-47 (2002).*
Benninghoff, PFOA slows breast Development in mice exposed via mom, Environmental Health news. <http://www.environmentalhealthnews.org/ehs/newscience/pfoa-impairs-breast-development-in-mice/>.*
Perfluorooctanoic acid, Case Studies in Science Policy. <http://www.defendingscience.org/case_studies/perfluorooctanoic-acid.cfm>.*
Cancer Health Center, WebMD 2010. <http://www.webmd.com/cancer/default.htm>.*
Abstract, Vredenburgh J J, Experience with irinotecan for the treatment of malignant glioma, Neuro-Oncology, 11(1 ):80-91, 2009.*
Melodelima et al, Treatment of esophageal tumors using high intensity ultrasound: first clinical results, Journal of Translational Medicine, 6:28, pp. 1-10, 2008.*
Shabalina et al., Carcinogenesis 20: 2237-2246 (1999).*
Ahmad et al., J Natl Cancer Inst 89(24): 1881-1886 (1997).*
Taylor, et al., "Insulin—like Effects of Fluoroacetate on Lipolysis and Lipogenesis in Adipose Tissue," Canadian Journal of Biochem., vol. 55, 1977.
Kees et al. Perfluorocarbon-Based Antidiabetic Agents (1992) J Med Chem 35, 944-953.
Trivedi et al. Perfluoro-N-[4-1H-tetrazol-5-ylmethyl)phenyl]-alkanamides. A New Class of Oral Antidiatetic Agents. (1989) J Med chem 32, 11-13.
Okochi et al. Perfluorooctanoic acid, a peroxisome-proliferating hypolipidemic agent, dissociates apolipoprotein B48 from lipoprotein particles and decreases secretion of very low density lipoproteins by cultured rat hepatocytes (1999) Biochimica Biophysica Acta 1437, 393-401.
Schedin et al. Reduced Cholesterol Accumulation and Improved Deficient Peroxisomal Functions in a Murine Model of Niemann-Pick Type C Disease upon Treatment with Peroxisomal Proliferators (1998) Biochem Pharm 56, 1195-1199.
Borges et al. Efect of the peroxisome proliferator perfluorodecanoic acid on growth and lipid metabolism in Sprague Dawley rats fed three dietary levels of selenium (1990) Arch Toxicology 1990, 26-30.
Cimini et al. Presence and inducibility of peroxisomes in a human glioblastoma cell line (2000) Biochimica Biophysica Acta 1474, 397-409.
Appleby et al. Structure of the human cyclo-oxygenase-2 gene (1994) Biochem J 302, 723-727.
Auboeuf et al. Tissue Distribution of Human PPARs (1997) Diabetes 46(8), 1319-1327.
Braissant et al. Differential Expression of Peroxisome Proliferator-Activated Receptors (PPARs): Tissue Distribution of PPAR-$\alpha$, -$\beta$, and -$\gamma$ in the Adult Rat (1996) Endocrinol 137(1), 354-366.
Brash et al. Discovery of a second 15.S-lipoxygenase in humans (1997) PNAS 94(12), 6148-6152.
Causevic et al. Substitution of a conserved amino acid residue alters the ligand binding properties of peroxisome proliferator activated receptors (1999) FEBS Letts. 463, 205-210.
Gelman et al. An update on the mechanisms of action of the peroxisome proliferator-activated receptors (PPARs) and their roles in inflammation and cancer (1999) Cell Mol Life Sci 55, 932-943.
GenBank Accession No. AF306566.
GenBank Accession No. M68874.
GenBank Accession No. NM003706.
GenBank Accession No. NM000963.
GenBank Accession No. NM001141.
GenBank Accession No. NM005090.
GenBank Accession No. NM021628.
GenBank Accession No. U63846.
GenBank Accession No. XM005818.
GenBank Accession No. XM008328.
Gilliland & Mandel. Mortality Among Employees of a Perfluorooctanoic Acid Production Plant (1993) J Occup Med 35(9), 950-954.
Hla & Neilson. Human cyclooxygenase-2 cDNA (1992) PNAS 89(16), 7384-7388.
Hla. Molecular Chracterization of the 5.2 KB Isoform of the Human Cyclooxygenase-1 Transcript (1996) Prostaglandins 51, 81-85.
Issemann & Green. Activation of a member of the steroid hormone receptor superfamily by peroxisome proliferators (1990) Nature 347, 645-650.
Jones et al. Molecular Cloning of Human Prostaglandin Endoperoxide Synthase Type II and Demonstration of Expression in Response to Cytokines (1993) J Biol Chem 268(12), 9049-9054.
Kersten et al. Roles of PPARs in health and disease (2000) Nature 405, 421-424.
Kliewer et al. Differential expression and activation of a family of murine peroxisome proliferator-activated receptors (1994) PNAS, 91, 7355-7359.
Kosaka et al. Characterization of the human gene (PTGS2) encoding prostaglandin-endoperoxide synthase 2 (1994) Eur J Biochem 221(3), 889-897.
Medicine abstracts.
Mukherjee et al. Identification, Characterization, and Tissue Distribution of Human Peroxisome Proliferator-activated Receptor (PPAR) Isoforms PPAR$\gamma$2 versus PPAR$\gamma$1 and Activation with Retinoid X Receptor Agonists and Antagonists (1997) J Biol Chem 272, 8071-8076.
Mukherjee et al. Human and Rat Peroxisome Proliferator Activated Receptors (PPARs) Demonstrate Similar Tissue Distribution but Different Responsiveness to PPAR Activators (1994) J Steroid Biochem Mol Biol 51, 157-166.
Palmer et al. cis-Parinaric acid is a ligand for the human peroxisome proliferator activated receptor $\gamma$: development of a novel spectrophotometric assay for the discovery of PPAR$\gamma$ ligands (1998) FEBS Letts. 431, 476-480.
Pickard et al. Molecular Cloning of Two New Human Paralogs of 85-kDa Cytosolic Phospholipase A2 (1999) J Biol Chem 274(13), 8823-8831.
Sharp et al. Molecular Cloning and Expression of Human Ca2+-sensitive Cytosolic Phospholipase A2 (1991) J Biol Chem 266(23), 14850-14853.
Underwood et al. A Novel Calcium-independent Phospholipase A2, cPLA2-$\gamma$, That is Prenylated and Contains Homology to cPLA2 (1998) J Biol Chem 273(34), 21926-21932.
Valentin et al. Cloning and Recombinant Expression of Human Group IIF-Secreted Phospholipase A2 (2000) Biochem Biophys Res Commun 279(1), 223-228.
Meridia® data sheet.
Finer & Walker (1999). Drug treatment of obesity, 1-17.
Abstract of JP 60001175.
Taylor et al (2002) Inflammation 26, 121-127.
Yang et al (2022) Biochemical Pharmacology 63, 1893-1900.
Panaretakis et al. (2001) Toxicology and Applied Pharmacology 173, 56-64.
Biegel et al. (2001) Toxicological Sciences 60, 44-55.
Yuki Ito and Tamie Nakajima; PPARcx-and DEHP-Induced Cancers; Accepted Jul. 8, 2008; 12pgs; Department of Occupational and Environment Health, Nagoya University Graduate School of Medicine, 65 Tsuramai-Cho, Showa-ku, Nagoya 466-8550, Japan.
Raymond M. David, Michael R. Moore, Dean C. Finney and Derek Guest; Chronic Toxicity of Di(2ethylhexyl)phthalate in Rats; Accepted Feb. 4, 2000; pp. 433-443; Health and Environment Laboratories, Eastman Kodak-Company, Rochester, New York 14652.

Wolfgang W. Huber, Bettina Grasi-Kraupp, and Rolf Schulte-Hermann; Hepatocarcinogenic Potential of Di(2-Ethylhexyl) phthalate in Rodents and its Implication on Human Risk; 1996; pp. 365-481.

Abdellatif, A.G. and Preat, V. 3, s.l.: Toxicology & Applied Pharmacology, 1991, vol. 111. 530-537.*The modulation of rat-liver carcinogenesis by perfluooroctanoic acid, a peroxisome proliferator*.

Alexander, B.H., et al. s.l.: Occupational & Environmental Medicine, 2003, vol. 60. 722-729.*Mortality of employees of a perfluorooctanesulphonyl fluoride manufacturing facility*.

Alexander, B.H. s.l.: USEPA, 2001.*Mortality study of workers employed at the 3M Cottage Grove facility*.

Anderson, M.E., et al. 1, s.l.: Toxicological Sciences, 2008, vol. 102. 3-14.*Perfluoroalkyl acids and related chemistries—Toxicokinetics and modes of action*.

Biegel, L.B., et al. s.l.: Toxicology & Applied Pharmacology, 1995, vol. 134. 18-25. *Effects of ammonium perfluorooctanoate on Leydig cell function: In vitro, in vivo, and ex vivo studies*.

Bjork, J.A. and Wallace, K.B. 1, s.l.: Toxicological Science, 2009, vol. 111. 89-99. *Structure-activity relationships and human relevance for perfluoralkyl acid-induced transcriptional activation of peroxisome proliferation in liver cell cultrures*.

Butenhoff, et al. s.l.: Toxicology, 2003, vol. 196. 95-116. *The reproductive toxicology of ammonium perfluorooctanoate (APFO ) in the rat*.

Butenhoff, J., et al. 1, s.l.: Toxicological Sciences, 2002, vol. 69. 244-257. *Toxicity of ammonium perfluorooctanoate in male cynomolgus monkeys after oral dosing for 6 months*.

Cattley, R.C., et al. s.l.: Regulatory & Toxicological Pharmacology, 1998, vol. 27. 47-60.*Do peroxisome proliferating compounds pose a hepatocarcinogenic hazard to humans*.

Chambers, K.T., Weber, S.M. and Corbert, J.A. s.l.: American Journal of Physiology, Endocrinology & Metabolism, 2007, vol. 292. E1052-E1061. *PGJ2-stimulated beta-cell apoptosis is associated with prolonged UPR activation*.

Cheung, C, et al. s.l.: Cancer Research, 2004, vol. 64. 3849-3854. *Diminished hepatocellular proliferation in mice humanized for the nuclear receptor peroxisome proliferator-activated receptor alpha*.

Cheung, H.H., et al. 12, s.l.: Experimental Cell Research, 2006, vol. 312. 2347-2357.*Involvement of caspase-2 and caspase-9 in endoplasmic reticulum stress-induced apaptosis: a role for the IAPs*.

Clegg, E.D., et al. 1, s.l.: Reproductive Toxicology, 1997, vol. 11. 107-121.*Leydig cell hyperplasia and adenoma formation: mechanisms and relevance to humans*.

Cook. J.C., et al. s.l.: Critical Reviews in Toxicology, 1999, vol. 29. 169-261.*Rodent leydig cell tumorigenesis: A review of the physiology, pathology, mechanisms, and relevance to humans*.

Cook, J.C., et al. s.l.: Toxicology & Applied Pharmacology, 1992, vol. 113. 209-217. *Introduction of Leydig cell adenomas by ammonium perfluorooctanoate: A possible endocrine related mechanism*.

Corton, J., et al. s.l.: Biochimie, 1997, vol. 79. 151-162. *Peroxisome proliferators alter the expression of estrogen-metabolising enzymes*.

Corton, J.C., Anderson, S.P. and Stauber, A. s.l.: Annual Review of Pharmacology and Toxicology, 2000, vol. 40. 491-518. *Central role of peroxisome proliferator-activated receptors in the actions of peroxisome proliferators*.

DeWitt, J.C., et al. 1, s.l..: Critical Reviews in Toxicology, 2009, vol. 39. 76-94.*Immunotoxicity of perfluorooctanoic acid and perfluorooctane sulfonate and the role of peroxisome proliferator-activated receptor alpha*.

Eagon, P.K., et al. s.l.: International Journal Cancer Research, 1994, vol. 58. 736-743.*Di(2-ethylhexyl)phthalate-induced changes in liver estrogen metabolism and hyperplasia*.

Ehresman, D.G. and Olsen, G. s.l.: Society of Toxicology Annual Meeting, 2005, vol. Abstract No. 1236. 253. *Evaluation of the half life (T1/2) of elimination of perfluorooctanoate (PFOA) from human serum*.

Elcombe, C.R. and Elcombe, B.M., s.l.: The Toxicologist, 2007, vol. 46th Annual Meeting. Abstract No. 867.*Characterization of hepatomegaly induced by ammonium perfluorooctanoic acid (APFO) in rats*.

Fan, L.Q., Cattley, R.C. and Corton, J.S. s.l.: Journal of Endocrinology, 1998, vol. 158. 237-246*Tissue specific induction of 17-beta-hydroxysteriod dehydrogenase type IV by peroxisome proliferator chemicals is dependent on the peroxisome proliferator-activated receptor alpha*.

Fernandez Freire, P., et al. 5, s.l.: Toxicology in Vitro, 2008, vol. 22. 1228-1233.*In vitro assessment of the cytotoxic and mutagenic potential of perfluorooctanoic acid*.

Gavin, C.E., et al. s.l.: Toxicologist, 1997, vol. 36. 1180. *Species differences in expression of pancreatic cholecystokinin-A receptors*.

Gavin, C.E., Martin, N.P. and Schlosser, M.J. s.l.: Toxicoloogist, 1996, vol. 30. 334.*Absence of specific CCK-A binding sites on human pancreatic membranes*.

Gibson, S.J. and Johnson, J.D. s.l.: Riker Laboratories Inc., Subsidiary of 3M, 1979 *Absorption of FC-143-14C in rats after a single oral dose*.

Gilliland, F.D. and Mandel, J.S. 5, s.l.: American Journal of Industrial Medicine, 1996, vol. 29. 560-568.*Serum perfluorooctanoic acid and hepatic enzymes, lipoproteins, and cholesterol: A study of occupationally exposed men*.

Griffith, F.D. and Long, J.E. 8 s.l.: American Industrial Hygiene Association Journal, 1980, vol. 41. 576-583. *Animal toxicology studies with ammonium perfluorooctanoate*.

Hanhijarvi, H., et al. s.l.: Pharmacology & Toxicology, 1987, vol. 61. 66-68.*Elimination and toxicity of perfluorooctanoic acid during subchronic administration in the wistar rat*.

Hanhijarvi, H, Ophaug, R.H. and Singer, L. 1, s.l.: Proceedings of the Society for Experimental Biology and Medicine, 1982, vol. 171. 50-55. *The sex-related difference in perfluorooctanoate and excretion in the rat*.

Harada, K., et al. 2, s.l.: Environmental Research, 2005, vol. 99. 253-261.*Renal clearance of perfluorooctane sulfonate and perfluorooctanoate in humans and their species-specific excretion*.

Harding, H.P. and Ron, D. s.l.: Diabetes, 2002, vol. 51. S455-461. *Endoplasmic reticulum stress and the development of diabetes*.

Healy, S.S., et al. s.l.: European Journal of Pharmacology, 2009, vol. Oct 14 epub.*Targeting the endoplasmic reticulum-stress response as an anticancer strategy*.

Hertz, R., Bisharashieban, J. and Bartana, J. s.l.: Journal of Biological Chemistry, 1995, vol. 270. 13470-13475. *Mode of action of peroxisome proliferators as hypolipidiemic drugs—Suppression of apolipoprotein CIII*.

Holzer, J., et al. 5, s.l.: International Journal of Hygiene & Environmental Health, 2009, vol. 212. 499-504.*One year follow-up of perfluorinated compounds in plasma of German residents from Arnsberg formerly exposed to PFOA-contaminated drinking water*.

Hu, X.Z. and Hu, D.C. s.l.: Archives Toxicology, 2009, vol. May 27 epub.*Effects of perfluorooctanoate and perfluorooctanesulfonate exposure on hepatoma HepG2 cells*.

J. Berger and Moller, D.E. s.l.: Annual Review of Medicine, 2002, vol. 53. 409-435.*The mechanisms of action of PPARs*.

Johnson, J.D., Gibson, S.J. and Ober, R.E. 6, s.l.: Fundamental and Applied Toxicology, 1984, vol. 4. 972-976. *Cholestyramine-enhanced fecal elimination of C-14 in rats after administration of ammonium C-14 perfluorooctanoate or potassium C-14 perfluorooctanesulfonate*.

Kennedy, G.L., et al. 4, s.l.: Critical Reviews in Toxicology, 2004, vol. 34. 351-384.*The toxicology of perfluorooctanoate*.

Kennedy, G.L. s.l.: Toxicology Letters, 1987, vol. 39. 295-300. *Increase in mouse liver weight following feeding of ammonium perfluorooctanoate and related fluorochemicals*.

Kim, R., et al. s.l.: Apoptosis, 2006, vol. 11. 5-13. *Role of the unfolded protein response in cell death*.

Klaunig, J.E., et al. s.l.: Critical Reviews in Toxicology, 2003, vol. 33. 655-780.*PPAR alpha agonist induced rodent tumours: Modes of action and human relevance*.

Kleszczynski, K. and Skladanowski, A.C. 3, s.l.: Toxicology Applied Pharmacology, 2009, Toxicol. Appl. Pharmacol. 234(3), vol. 234, 300-305. *Mechanism of cytotoxic action of perfluorinated acids. I. Alteration in plasma membrane potential and intracellular pH level*.

Koeffler, H.P. s.l.: Clinical Cancer Research, 2003, vol. 9. 1-9. *Peroxisome proliferator-activated receptor gamma and cancers*.

Kudo, N., et al. 3, s.l.: Chemico Biological Interactions, 2002, vol. 139. 301-316.*Sex-hormone regulated renal transport of perfluorooctanoic acid*.

Kuslikis, B.I., Vanden Heuvel, J.P. and Peterson, R.E. 1, s.l. : Journal of Biochemical Toxicology, 1992, vol. 7. 25-29. *Lack of evidence for perfluorodecanoyl- or perfluorooctanoyl-coenzyme A formation in male and female rats.*

Lee, A.H. and Glimcher, L.H. s.l. : Cellular and Molecular Life Sciences, 2009, vol. 66. 2835-2850.*Intersection of the unfolded protein response and hepatic lipid metabolism.*

Lee, A.H., et al. s.l. : Science, 2008, vol. 320. 1492-1496. *Regulation of hepatic lipogenesis by the transcription factor XBP1.*

Liu, R.C.M., et al. s.l. : Fundamental & Applied Toxicology, 1996, vol. 30. 220-228.*Effect of the peroxisome proliferator, ammonium perfluorooctanoate (APFO), on hepatic aromatase activity in adult male Crl:CDBR (CD) rats.*

Liu, R.C.M., Hahn, C and Hurtt, M.E. s.l. : Fundamental & Applied Toxicology, 1996, vol. 30. 102-108.*The direct effect of hepatic peroxisome proliferators on rat Leydig cell function in vitro.*

Marciniak, S.J. and Ron, D. s.l. : Physiological Reviews, 2006, vol. 86. 1133-1149.*Endoplasmic reticulum stress signalling in disease.*

Morimura, K. et al. s.l. : Carcinogenesis, 2006, vol. 27. 1074-1080. *Differential susceptibility of mice humanized for peroxisome proliferator-activated receptor to WY14,643-included liver tumorigenesis.*

N.G., Ordonez, 3, s.l. : Advances in Anatomic Pathology, 2001, vol. 8. 144-159. *Pancreatic acinar cell carcinoma.*

Nakagawa, H., et al. s.l. : Basic Clinical Pharmacology & Toxicology, 2009, vol. Apr3 epbu.*Human organic anion transporter hOAT4 is a transporter of perfluorooctanoic acid.*

Obourn, J.D., et al. s.l. : Toxicology & Applied Pharmacology, 1997, vol. 145. 425-436.*Mechanisms for the pancreatic oncogenic effects of the peroxisome proliferator Wyeth-14,643.*

Ohmori, K., et al. s.l. : Toxicology, 2003, vol. 184. 135-140. *Comparison of the toxicokinetics between perfluorocarboxylic acids with different carbon chain length.*

Olsen, G.W. and Burris, J.M. 4, s.l. : Drug and Chemical Toxicology, 2000, vol. 23. 603-620.*Plasma cholecystokinin and hepatic enzymes, cholesterol and lipoproteins in ammonium perfluorooctanoate production workers.*

Olsen, G.W., et al. 7, s.l. : Journal of Occupational and Environmental Medicine, 1998, vol. 40. 614-622.*An epidemiologic investigation of reproductive hormones in men with occupational exposure to perfluorooctanoic acid.*

Olsen, G.W., et al. s.l. : Journal of Occupational & Environmental Medicine, 2003, vol. 45. 260-270. *Epidemiological assessment of worker serum perfluorooctanesulfonate (PFOA) and pertlouroocianoate concentrations and medical surveillance examinations.*

Pandol, S.J. Eds: M. Sleisenger & J.S. Fortran, s.l. : Gastrointestinal and liver diseases, 1998, vol. 1. 771-782. *Pancreatic physiology and secretory testing.*

Perkins, R.G. and Butenhoff, J.L. 4, s.l. : Drug and Chemical Toxicology, 2004, vol. 27. 361-378. *13-week dietary toxicity study of ammonium perfluorooctanoate (APFO) in male rats.*

Permadi, H., et al. 6, s.l. : Biochemical Pharmacology, 1992, vol. 44. 1183-1191.*Effects of perfluoro fatty acids on xenobiotic-metabolizing enzymes, enzymes which detoxify reactive forms of oxygen and lipid peroxidation in mouse liver.*

Reddy, J.K. and Rao, M.S. s.l. : Journal of National Cancer Institute, 1977, vol. 59. 1645-1650.*Malignant tumors in rats fed nafenopin, a hepatic peroxisome proliferator.*

Ren, H., et al. 3-4, s.l. : Reproductive Toxicology, 2009. vol. 27. 266-277.*Evidence for the involvement of xenobiotic-responsive nuclear receptors in transcriptional effects upon perfluoroalkyl acid exposure in diverse species.*

Riker, Aug. 29, 1987, s.l. : USEPA, 1987. vol. Experiment No. 0281CR0012. *Two year oral (diet) toxicity/carcinogenicity study of fluorochemical FC-143 in rats.*

Rosen, M.B., et al. 1, s.l. : Toxicological Sciences, 2008, vol. 103. 46-56. *Toxicogenomic dissection of the perfluorooctanoic acid transcript profile in mouse liver: Evidence for the involvement of nuclear receptors PPARalpha and CAR.*

Sakr, C.J., et al. 10, s.l. : Journal of Occupational & Environmental Medicine, 2007, vol. 49. 1086-1096. *Cross-sectional study of lipids and liver enzymes related to serum biomarker of exposure (ammonium perflurorooctanoate or APFO) as part of a general health survey in a cohort of occupationally exposed workers.*

Sakr, C.J., et al. s.l. : Occupational & Environmental Medicine, 2009, vol. Jun 23 epub.*Ischemic heart disease mortality among workers with occupational exposure to ammonium perfluorooctanoate.*

Schroder, M. 6, s.l. : Cell & Molecular Life Sciences, 2008, vol. 65. 862-894.*Endoplasmic reticulum stress responses.*

Shi, Y.H., Hon, M. and Evans, R.M. s.l. : Proceedings of the National Academy of Sciences of the USA, 2002, vol. 99. 2613-2618. *The peroxisome proliferator-activated receptor delta, an integrator of transcriptional repression and nuclear receptor signaling.*

Staels, B. and Auwerz, J. s.l. : Current Pharmaceutical Design, 1997. vol. 3. 1-14.*Role of PPAR in the pharmacological regulation of lipoprotein metabolism by fibrates and thiazolidinediones.*

Szegezdi, E., et al. 9, s.l. : EMBO Journal, 2006, vol. 7. 880-885. *Mediators of endoplasmic reticulum stress-in-duced apoptosis.*

Takacs, M.L. and Abbott, B.D. 1, s.l. : Toxicological Sciences, 2007, vol. 95. 108-117.*Activation of mouse and human peroxisome proliferator-activated receptors (alpha, beta/delta, gamma) by perfluorooctanoic acid and perfluorooctance sulfonate.*

Ubel, F.A., Sorenson, S.D. and E.E., Roach. 8, s.l. : American Industrial Hygiene Association Journal, 1980, vol. 41. 584-589.*Health-status of plant workers exposed to fluorochemicals—a preliminary report.*

Upham, B.L., et al. 4, s.l. : Environmental Health Perspectives, 2009, vol. 117. 545-551.*Structure-activity-dependent regulation of cell communication by perfluorinated fatty acids using in vivo and in vitro model systems.*

USEPA. s.l. : Office of Pollution Prevention and Toxics Risk Assessment Division, 2005.*US Environmental Protection Agency, Draft Hazard Assessment of Perfluorooctanoic acid and its salts.*

Vanden Heuval, J.P., et al. 2, s.l. : Journal of Biochemical Toxicology, 1991, vol. 6. 83-92.*Tissue distribution, metabolism, and elimination of perfluorooctanoic acid in male and female rats.*

Vanden Heuval, J.P., at al. s.l. : Toxicological Sciences, 2006, vol. 92. 476-486. *Differential activation of nuclear receptors by perfluorinated fatty acid analogs and natural fatty acids: A comparison of human, mouse, and rat peroxisome proliferator-activated receptor-alpha, -beta, and -gamma, LXR-beta, and RXR-alpha.*

Vazquez, M. Silvestre, J.S. and Prous, J.R. s.l. : Methods and Findings in Experimental and Clinical Pharmacology, 2002, vol. 24. 515-523.*Experimental approaches to study PPAR gamma agonists and antidiabteic drugs.*

Vosper, H., et al. 47, s.l. : The Journal of Biological Chemistry, 2001, vol. 276. 44258-44265.*The peroxisome proliferator-activated receptor delta promotes lipid accumulation in human macrophages.*

Vu-Dac, N, et al. s.l. : Journal of Clinical Investigation, 1995, vol. 96. 741-750. *Fibrates increase human apolipoprotein AIII expression through activation of the peroxisome proliferation-activated receptor.*

Weber, S.M. et al. s.l. : American Journal of Physiology, Endocrinology & Metabolism, 2004, vol. 287. E1171-E1177. *PPARgamma ligands induce ER stress in pancreatic beta-cells: ER stress activation results in attenuation of cytokine signaling.*

White, S.S., et al. 3-4, s.l. : Reproductive Toxicology, 2009, vol. 27. 289-298.*Effects of perfluorooctanoic acid on mouse mammary gland development and differentiation resulting from cross-foster and restricted gestational exposures.*

Wu, L.L., et al. 31, s.l. : BMC Structural Biology, 2009, vol. 9. 1-7. *Interaction of perfluorooctanoic acid with human serum albumin.*

Yang, C, et al. 3-4, s.l. : Reproductive Toxicology, 2009, vol. 27. 299-306.*Differential effects of peripubertal exposure to perfluorooctanoic acid on mammary gland development in C57/Bl/6 and Balb/c mouse strains.*

Yang, Q. and Xie, Y: Depierre, J.W. 2, s.l. : Clinical and Experimental Immunology, 2000, vol. 122. 219-226. *Effects of peroxisome proliferators on the thymus and spleen of mice.*

Yang, Q., et al. s.l. : Biochemical Pharmacology, 2001, vol. 62. 1133-1140.*Further evidence for the involvement of inhibition of cell proliferation and development in thymic and splenic atrophy induced by the peroxisome proliferator PFOA in mice.*

Yang, Q., et al. s.l. : International Immunopharmacology, 2002, vol. 2. 389-397.*Potent suppression of the adaptive immune response in mice upon dietary exposure to the potent peroxisome proliferator, perfluorooctanoic acid.*

Zang, C., et al. 8, s.l. : Molecular Cancer Therapy, 2009, vol. 8. 2296-2307. *Induction of endoplasmic reticulum stress response by TZD18, a novel dual ligand for peroxisome proliferator-activated receptor alpha-gamma, in human breast cancer cells.*

Zhang, K.: Kaufman, R.J. s.l. : Nature, 2008, vol. 454. 455-462. *From endoplasmic-reticulum stress to the inflammatory response.*

Permaldi et al. (1993) Xenobiotica 23(7): 761-770.

Abdellatif et al. (1990) Carcinogenesis 11(11): 1899-1902.

Intrasuksri et al. (1998) Gen. Pharmacol. 31(2): 187-197.

Maloney & Waxman (1999) Toxicol. App. Pharm. 161: 209-218.

Shabalina et al. (1999) Carcinogenesis 20: 2237-2246.

Nilsson et al. (1991) Chemico-Biological Inventions 78, 235-250.

State of New Jersey Department of Environmental Protection; Alan Stern, DABT, Chief Risk Analysis Section, DSRT and Eileen Murphy, Director, DSRT, Guidance for PFOA in Drinking Water at Pennsgrove Water Supply Company; pp. 1-12.

American Council on Science and Health: The top ten unfounded health scares of 2006:6; Teflon contains a cancer causing chemical (PFOA); Dec. 2006; pp. 1-2.

Knight et al. (2005) Which drugs cause cancer? Education and debate; Animal tests yield misleading results 5, pp. 477-479.

O'Dwyer and Price (2005) Pill and HRT drugs cause cancer, say researchers, pp. 1-2.

Ellison (2005) Cholesterol lowering drugs and cancer, pp. 1-3.

Voigt (2005) Methods of Molecular Medicine 110, 39-48 (abstract).

Boyd, M.R.; The NCI in vitro anti-cancer drug discovery screen concept, implementation and operation 1985-1995, pp. 23-40.

Xie et al. (2002) Lipids 37(2), pp. 139-146.

Van Rafelghem et al. (1988) Toxicology Letters 40, pp. 57-69.

Freshney (1983) Culture of Animal Cells, A Manual of Basic technique, Alan R. Liss, Inc., New York, p. 4.

Dermer (1994) Biotechnology 12: p. 230.

Gura (1997) Science 278, pp. 1041-1042.

The Jere Beasley Report, Feb. 2005.

The Cancer Blog (2006); FDA's Teflon carcinogen warning getting stronger.

www.msnbc.com (2005); Teflon cancer risks downplayed?

The Oxford Dictionary of Biochemistry and Molecular Biology (2000) (extract).

www.wordnet.princeton.edu/perl/webwn (2006) (extract).

Johnson et al. (2001) British Journal of Cancer 84(10), pp. 1424-1431.

Davis et al. (1991) Lipids 26(10), pp. 857-859.

Adam, M et al. Cancer Res 2006 66(7):3828-35. *Targeting PIM kinases impairs survival of hematopoietic cells transformed by kinase inhibitorsensitive and kinase inhibitor-rseistant forms of Fms-like tyrosine kinase and BCR/ABL.*

Amaravadi, R and Thompson. CB. J Clin Invest 2005 115(10):2618-24. *The survival kinases Akt and PIM as potential pharmacological targets.*

Beier, Uh et al. In! J Oncol2007 30(6) :1381-7. *Overexpression of PIM-1 in head and neck squamous cell carcinomas.*

Brault, Let al. Haematologica Feb. 9, 2010 epub. *PIM serine/threonine kinases in pathogenesis and therapy of haematological malignancies and solid cancers.*

Chiang, WF et al. Int J Oral Maxillofac Surg 2006 35(8) :740-5. *Upregulation of a serine-threonine kinase proto-oncogene PIM-1 in oral squamous cell carcinoma.*

Choi, JY; et al. J Otolaryngol Head Neck Surg 2010 39(1):28-34. *Clinical significance ofthe expression of galectin-3 and PIM-1 in laryngeal squamous cell carcinoma.*

Chen, WW et al. Mol Cancer Res 2005 3(8):443-51 . *PIM family kinases enhance tumour growth of prostate cancer cells.*

Chen, J et al. Am J Pathol 2009, 175(10):400-11. *Hypoxia-mediated upregulation of PIM-1 contributes to solid tumour formation.*

Chen, JL et al. Blood 2008, 111(3):1677-85. *PIM-1 and PIM-2 kinases are required for efficient pre-B-cell transformation by v-Abi oncogene.*

Cibull, TL et al. J. Clin. Pathol. 200659(3): 285-8. *Overexpression of PIM-1 during progression of prostatic adenocarcinoma.*

Cohen, AM et al. Leuk Lymphoma 2004 45(5):951-5. *Increased expression of hPIM-2 gene in human chronic lymphocytic leukemia and non-Hodgkin lymphoma.*

Dai, H, et al. Prostate 2005, 65(3):276-86. *PIM-2 upregulation: biological implications associated with disease progression and perineueral invasion in prostate cancer.*

Fuji, C et al. Int J Cancer 2005 114(2):209-18 .. *Expression of serine/threonine kinase PIM-3 in hepatocellular carcinoma development and its role in proliferation of human hepatoma cell lines.*

Gong, J; et al. J Surg Res 2009153(1):17-22. *Serine/threonine kinase PIM-2 promotes liver tumourigenesis induction through mediating survival and preventing apoptosis of liver cell.*

Hammerman, PS et al. Blood 2005 105(11 ):4477-83. *PIM and Akt oncogenes are independent regulators of hematopoietic cell growth and survival.*

He HC, et al. Chin Med J (Engl). Sep. 5, 2007 ;120(17):1491-3. Detection of PIM-1 mRNA in prostate cancer diagnosis.

Hogan, C; et al. J Bioi Chern 2008, 283(26):18012-18023. *Elevated levels of oncogenic protein kinase PIM-1 induce the p53 pathway in cultured cells and correlate with increased MDM2 in mantle cell lymphoma.*

Kim, KT et al. Blood 2005,105(4):1759-67. *PIM-1 is upregulated by constitutively activated FL T3 and plays a role in Flt3-mediated cell survival.*

Li, YV et al. Cancer Res 2006 66(13):6741-7. *PIM-3, a proto-oncogene with serinelthreonine linase activity, is aberrantly expressed in human pancreatic cancer and phosphotylates bad to block bad-mediated apoptosis in human pancreatic cancer cell lines.*

Li YV, et al. Cancer Sci. 2009 Mar;100(3):396-404. Epub Dec. 16, 2008. *Essential contribution of Ets-1 to constitutive PIM-3 expression in human pancreatic cancer cells.*

Lin, YW et al. Blood 2010, 115(4):824-33. *A small molecule inhibitor of PIM protein kinases blocks the growth fo precursos T-cell lymphoblastic leukemia/lymphoma.*

Moenner, M et al. Cancer Res, 2007, vol. 67. 10631-10634. *Integrated Endoplasmic Reticulum Stress Responses in Cancer.*

Mumenthaler, SM et al. Mol Cancer Ther. 20098(10):2882-93. *Pharmacologic inhibition of PIM kinases alters prostate cancer cell grow1h and resensitizes chemoresistant cells to taxanes.*

Nga, ME et al. Int J Exp Patho12010, 91(1):34-43. *PIM-1 kinase expression in adipocytic neoplasms: diagnostic and biological implications.*

Popivanova, BK et al. Cancer Sci 2007 98(3):321-8. *Proto-oncogene, PIM-3 with serine/threonine kinase activity, is aberrantly expressed in human colon cancer cells and can prevent Bad-mediated apoptosis.*

Reiser-Erkan, C et al. Cancer Bioi Ther 2008, 7(9) :1352-9. *Hypoxiainducible proto-oncogene PIM-1 is a prognostic marker in pancreatic ductal adenocarcinoma.*

Roh, M et al. PLoS One 2008, 3(7):32572. *A role for polyploidy in the tumourigenicity of PIM-1 expressing human prostate and mammary epithelial cells.*

Shah, Net al. P Eur J Cancer 2008 44(15):2144-51 . *Potential roles for the PIM1 kinase in human cancer—a molecular and therapeutic appraisal.*

Strasser, A and Puthalakath, H: Cell Death and Differentiation, 2008, vol. 15. 223-225. *Fold up or perish: unfolded protein response and chemotherapy.*

Warnecke-Eberz U, et al. Anticancer Res. Nov. 2009; 29(11):4451-5. *Prognostic impact of protein overexpression of the proto-oncogene PIM-1 in gastric cancer.*

Wolf, C et al: Toxicological Sciences, 2008, vol. 106. 162-171 . *Activation of Mouse and Human Peroxisome Proliferator—Activated Receptor Alpha by Perfluoralkyl Acids of Different Functional Groups and Chain Lengths.*

Wu, Y et al. Oncogene Jan. 18, 2010, epub. *Accelerated hepatocellular carcinoma development in mice expressing the PIM-3 transgene selectively in the liver.*

Xu Y, et al. J Surg OncoL Dec. 2005 92(4): 326-330. *Overexpression of PIM-1 is a potential biomarker in prostate carcinoma.*

Zheng, HC et al. J Cancer Res Clin Oncol 2008 134(4):481-8. *Aberrant PIM-3 expression is involved in gastric adenoma-adenocarcinoma sequence and cancer progression.*

Sahin et al., Epigalocatechin-3-gallate activates Nrf2/HO-1 signaling pathway in cisplatin-induced nephrotoxicity in rats, Life Sciences, 87, 240-245, 2010.

Wolf et al., Toxicological Sciences 106(1), pp. 162-171 (2008).

Meridia data sheet (http://www.rxabbott.com/pdf/meridia.pdf) (2002).

MacPherson et al., EJC Supplements 8(7), p. 124 (2010).

Barnett et al., EJC Supplements 8(7), pp. 45-46 (2010).

Lou et al., Toxicological Sciences 107(2), pp. 331-341 (2009).

Heerdt et al., Cancer Research 54, pp. 3288-3294 (1994).

Fukuoka et al, Nippon Rinsho 54(1), pp. 250-258 (English abstract) (1996).

Shitara, "Application of anti-ganglioside humanized antibodies for immunotherapy of malignant melanoma & lung cancer", Igaku No Ayumi 195; pp. 91-95 (English Abstract) (2000).

Singh et al., "Dysfunctional KEAP1-NRF2 Interaction in Non-Small-Cell Lung Cancer", PLoS Med 3(10): e420. DOI: 10.1371/journal.pmed.0030420, pp. 1865-1876 (2006).

Li et al., "KEAP1 gene mutations and NRF2 activation are common in pulmonary papillary adenocarcinoma", J Hum Genet. 56(3):230-4 (2011).

Therasse et al,, "New guidelines to evaluate the response to treatment in solid tumors", Jour Nat Cance Inst. vol. 92, No, 3, pp. 205-216 (2000).

Postel-Vinay et al., "Clinical benefit in phase-1 trials of novel molecularly targeted agents: does dose matter?", Brit. Jour. Cancer, 100(9), pp. 1373-1378 (2009).

Eisenhauer et al., New response evaluation criteria in solid tumours: revised RECIST guideline (version 1.1), Euro. Jour Cancer 45, pp. 228-247 (2009).

Appendix II: RECIST response criteria for solid tumours.

* cited by examiner wherein X represents hydrogen or fluorine.

Part 1 of 3

Part 2 of 3

Part 3 of 3

TREATMENT OF CANCER BY ADMINISTRATION OF PERFLUOROOCTANOIC ACID

This invention relates to the medical use of compounds, and to methods of identifying further useful compounds, particularly in the treatment of diabetes, obesity, hyperlipidaemia, hypercholesterolaemia, atherosclerosis, cancer and inflammation, or other conditions where alterations in lipid or eicosanoid status may be desirable.

Perfluorooctanoic acid (PFOA) and other perfluorinated fatty acids or fluoroalkyl molecules are synthetic molecules used in industrial applications, principally as surfactants. The effects of these compounds on laboratory animals and cells has been studied, as have the effects of occupational exposure in humans (see, for example, Gilliland & Mandel (1993) *J Occup Med* 35(9), 950-954; Kees et al (1992) *J Med Chem* 35, 944-953). U.S. Pat. No. 4,624,851 suggests treatment of symptoms of cancer using fluorine containing acids; no experimental data is presented.

We have surprisingly found that such compounds may have beneficial effects. We have found that such compounds may be useful in treatment of diabetes, obesity, hyperlipidaemia, hypercholesterolaemia, atherosclerosis, cancer and inflammation, or other conditions where alterations in lipid or eicosanoid status may be desirable.

A first aspect of the invention provides a method of treatment of a patient in need of modulation (preferably reduction) of body mass or modulation (preferably prevention or reduction) of increase in body mass, and/or in need of modulation (preferably reduction) of plasma insulin, plasma glucose, plasma triglycerides and/or plasma cholesterol, comprising administering to the patient an effective amount of a compound of formula I as defined herein. The compound of formula I is $$Z^1—X—Z^2 \qquad \text{I}$$

wherein $Z^1$ represents —$CO_2H$ or a derivative thereof;
$Z^2$ represents F, H, —$CO_2H$ or a derivative thereof; and
X represents fluorinated alkylene; or a solvate thereof; which compounds are referred to hereinafter as "the compounds of the invention".

A further aspect of the invention provides a method of treatment of a patient in need of an antitumour agent or an antiinflammatory agent, or in need of modulation in lipid or eicosanoid status, comprising administering to the patient an effective amount of a compound of formula I as defined herein. A compound of formula I is considered to be effective as an antitumour agent or an anfiinflammatory agent or in modulating lipid or eicosanoid status (ie type and concentration of lipid or eicosanoid, either systemically or in a particular locus or tissue).

The patient may be a patient with or at risk of excessive inflammation, for example with or at risk of arthritis, or a patient with or at risk of developing a tumour. The compound may reduce the development, growth or metastasis of a tumour.

The compound may be useful in treating any condition or disorder in which the patient has or is at risk of excessive inflammation. The patient may have an allergic or autoimmune disease. The patient may have, for example, psoriasis, inflammatory bowel disease, asthma or rheumatism.

A further aspect of the invention provides a method of treatment of a patient who is overweight or obese and/or has diabetes, hyperlipidaemia, atherosclerosis, coronary heart disease, stroke, obstructive sleep apnoea, arthritis (for example osteoarthritis) and/or reduced fertility, or is at risk of developing such a condition, comprising administering to the patient an effective amount of a compound of formula I as defined herein.

A further aspect of the invention provides a method of treatment of a patient in need of modulation of PPAR (for example PPARα, δ or γ) activity, comprising administering to the patient an effective amount of a compound of formula I as defined herein. The compound may be a PPAR agonist or a PPAR antagonist; it may be an agonist for one PPAR and an antagonist for a different PPAR. Preferably the patient is in need of an increase in PPARα or PPARγ activity and the compound is a PPARα or PPARγ agonist. Alternatively, the patient may be in need of a decrease in PPARα or PPARγ activity and the compound may be a PPARα or PPARγ antagonist. In a further alternative, the patient may be in need of an increase in PPARδ activity and the compound is a PPARδ agonist. In a still further alternative, the patient may be in need of a decrease in PPARδ activity and the compound may be a PPARδ antagonist. PPARδ may have opposing effects to PPARα or PPARγ (see, for example, WO01/07066).

A further aspect of the invention provides a method of treatment of a patient in need of modulation of lipid or eicosanoid status or function, for example in need of modulation of the activity of a lipid metabolising or binding entity (including a lipid metabolising enzyme and a lipid binding polypeptide, for example a lipid transporting polypeptide), for example cycloxygenase (for example cyclooxygenase I or cyclooxygenase II) activity or phospholipase A (for example phospholipase A2) or lipoxygenase, comprising administering to the patient an effective amount of a compound of formula I as defined herein. Preferably the patient is in need of a decrease in a lipid metabolising or binding activity, for example cycloxygenase (for example cyclooxygenase I or cyclooxygenase II) activity or phospholipase A or lipoxygenase and the compound is an inhibitor of such activity. For example, inappropriate lipoxygenase activity may be involved in inflammation, hypersensitivity, asthma and some vascular diseases; thus a decrease in a lipoxygenase activity may be useful in such a condition.

Alternatively, the patient may be in need of an increase in such activity and the compound may be an activator of such activity.

Further preferences in relation to the patient and compound are indicated below.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

When referred to herein, derivatives of —$CO_2H$ groups include groups which are commonly derived from a carboxylic acid and/or groups that contain a central carbon atom (i.e. the carbon atom that is attached to X) that is at the same oxidation state as —C(O)OH. Derivatives of —CO$_2$H groups therefore includes groups such as:
(i) esters, e.g. those formed with an alcohol of formula R$^1$OH, wherein R$^1$ represents aryl or alkyl;
(ii) thioesters, e.g. those formed with a thiol of formula R$^1$SH, wherein R$^1$ is as hereinbefore defined; and
(iii) salts, e.g. those formed with a nitrogen-containing base such as ammonia, an alkylamine, a dialkylamine, a trialkylamine and pyridine or alkali or alkaline earth metal salts (e.g. Na, K, Cs, Mg or Ca salts).

Preferred derivatives of —CO$_2$H groups include those that are pharmaceutically acceptable.

Where the term fluorine is used herein, it is intended (where appropriate) that reference to other halogens, for example chlorine or bromine or more than one halogen, is included. However, it is strongly preferred that the halogen is fluorine.

It is preferred that the compound of Formula I comprises at least two fluorine atoms, preferably at least three, four, five, six, seven or eight fluorine atoms.

The term "aryl", when used herein, includes C$_{6-10}$ aryl groups such as phenyl, naphthyl and the like. Aryl groups may be substituted by one or more substituents including —OH, cyano, halo, nitro, amino, alkyl and alkoxy. When substituted, aryl groups are preferably substituted by between one and three substituents.

The term alkyl, when used herein, refers to alkyl groups of 1 to 16, preferably 1 to 10 (e.g. 1 to 6) carbon atoms.

The term alkoxy, when used herein, refers to alkoxy groups of 1 to 16, preferably 1 to 10 (e.g. 1 to 6) carbon atoms.

Alkyl and alkoxy groups as defined herein may be straight-chain or, when there is a sufficient number (i.e. a minimum of three) of carbon atoms, be branched-chain and/or cyclic and/or heterocyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated and/or interrupted by one or more oxygen and/or sulfur atoms. Alkyl and alkoxy groups may also be substituted by one or more halo, and especially fluoro, atoms.

The term "halo", when used herein, includes fluoro, chloro, bromo and iodo.

The terms alkylamine, dialkylamine and trialkylamine, when used herein, refer to amines bearing one, two or three alkyl groups as defined herein, respectively.

The term alkylene, when used herein, refers to alkylene groups of 1 to 20, preferably 2 to 17 (e.g. 6 to 12) carbon atoms. Alkylene groups may be straight-chain or, when there is a sufficient number (i.e. a minimum of two or three, as appropriate) of carbon atoms, be branched-chain and/or cyclic and/or heterocyclic. Further, when there is a sufficient number (i.e. a minimum of four) of carbon atoms, such alkylene groups may also be part cyclic/acyclic. Such alkylene chains may also be saturated or, when there is a sufficient number (i.e. a minimum of two) of carbon atoms, be unsaturated and/or interrupted by one or more oxygen and/or sulfur atoms.

Preferred compounds of formula I include those in which:
alkylene group X is at least 50% fluorinated;
alkylene group X contains between 2 and 17 carbon atoms;
Z$^1$ represents —CO$_2$H, an ammonium, (C$_{1-10}$ alkyl)ammonium, di-(C$_{1-10}$ alkyl)ammonium or tri-(C$_{1-10}$ alkyl)ammonium salt of —CO$_2$H, or —CO$_2$R$^1$;
Z$^2$ represents F, H, —CO$_2$H or —CO$_2$R$^1$;
R$^1$ represents C$_{1-6}$ alkyl.

More preferred compounds of formula I include those in which:
alkylene group X is at least 75% fluorinated;
alkylene group X is straight-chain, saturated and contains between 4 and 14 carbon atoms;
Z$^1$ represents —CO$_2$H, an ammonium, (C$_{1-6}$ alkyl)ammonium, di-(C$_{1-6}$ alkyl)ammonium or tri-(C$_{1-6}$ alkyl)ammonium salt of —CO$_2$H, or —CO$_2$R$^1$;
Z$^2$ represents F, —CO$_2$H or —CO$_2$R$^1$;
R$^1$ represents straight-chain, unsubstituted, saturated C$_{1-4}$ alkyl.

Even more preferred compounds of formula I include those in which:
alkylene group X is at least 90% fluorinated;
alkylene group X is straight-chain, saturated and contains between 6 and 12 carbon atoms;
Z$^1$ represents —CO$_2$H, an ammonium salt of —CO$_2$H, or —CO$_2$R$^1$;
R$^1$ represents straight-chain, unsubstituted, saturated C$_{1-2}$ alkyl.

Particularly preferred compounds of formula I may be or comprise a member of the following group:
Perfluoroheptanoic acid; perfluorooctanoic acid; perfluorononanoic acid; perfluorodecanoic acid; perfluoroundecanoic acid; perfluorododecanoic acid; perfluorotetradecanoic acid; perfluorohexadecanoic acid; perfluorooctadecanoic acid; perfluorosuccinic acid; perfluoroglutaric acid; perfluoroadipic acid; perfluorosuberic acid; perfluoroazelaic acid; perfluorosebacic acid; perfluoro-1,10-decanedicarboxylic acid;
methyl perfluoroheptanoate; methyl perfluorooctanoate; methyl perfluorononanoate; methyl perfluorodecanoate; methyl perfluoroundecanoate; methyl perfluorododecanoate; methyl perfluorotridecanoate; methyl perfluorotetradecanoate; methyl perfluoropentadecanoate; methyl perfluorohexadecanoate; methyl perfluorooctadecanoate;
dimethyl perfluorosuccinate; dimethyl perfluoroglutarate; dimethyl perfluoroadipate; dimethyl perfluorosuberate; dimethyl perfluoroazelate; dimethyl perfluorosebacate; perfluoro-1,10-decanedicarboxylic acid, dimethyl ester; and dimethyl perfluorododecanedioate.

These compounds may be obtained from any suitable supplier, for example 3M, DuPont, Miteni or Dyneon.

Examples of fluoroalkyl carbonyl compounds that may be useful include alpha-branched fluoroalkylcarbonyl fluorides and derivatives thereof, as described in U.S. Pat. No. 6,013,795 or U.S. Pat. No. 6,015,838 (both incorporated herein by reference) and references given therein, for example U.S. Pat. No. 2,567,011 (incorporated herein by reference). Methods of preparing same are also described. These compounds may also be useful in the synthesis of further compounds of the invention.

It is preferred that the compound is not a compound as discussed in U.S. Pat. No. 6,028,109, which are indicated to be PPAR agonists. Thus, it is preferred that the compound is not a compound represented by formula (I) of U.S. Pat. No. 6,028,109 (shown in FIG. 8).

Particularly preferred compounds of formula I include fluorinated fatty acids, such as perfluorinated fatty acids, for example perfluorooctanoic acid (PFOA) or a derivative or pharmaceutically acceptable salt or ester thereof (e.g. ammonium perfluorooctanoate (APFO)). The chemical formula for APFO is CF$_3$(CF$_2$)$_6$COO$^-$NH$_4^+$ (octanoic acid, pentadecafluoro-, ammonium salt; C-8, FC-143; CAS Registry No 3825-26-1). It may be obtained from DuPont (DuPont Chemical Solutions Enterprise, DuPont-Strassel, D-61343 Bad Homburg, Germany). Common contaminants of APFO include ammonium perfluoroheptanoate (CAS 6130-43-4), ammonium perfluorohexanoate (CAS 68259-11-0), ammonium perfluoropentanoate (CAS 21615-47-4), and branched chain homologs that are generically known as ammonium perfluoroisooctanoate, ammonium perfluoroisoheptanoate, ammonium perfluoroisohexanoate and ammonium perfluoroisopentanoate. Whilst it is considered that the effects observed in Example 1 using an APFO preparation arise from the administration of APFO itself, it will be appreciated that one or more contaminants, for example one or more of the possible contaminants listed above, may contribute to the effects observed.

It is preferred that the compound is not PFOS (perfluorooctylsulphonate) or perfluorodecanoic acid or a derivative or salt or ester thereof; these compounds may have toxic or environmentally undesirable effects.

It is preferred that the compound of formula I (or identified or identifiable by a screening method of the invention, as discussed below) is metabolically stable; for example it is preferred that the compound has a similar rate of metabolism to perfluorooctanoic acid. The compound may be considered to be a lipid mimetic which may be metabolically stable.

A further aspect of the invention provides the use of a compound of formula I as defined herein in the manufacture of a medicament for the treatment of a patient in need of modulation (preferably reduction) of body mass or modulation (preferably prevention or reduction) of increase in body mass, and/or in need of modulation (preferably reduction) of plasma insulin, plasma glucose, plasma triglycerides, leptin and/or plasma cholesterol. The patient may (for example in relation to a decrease in the above-listed parameters) be overweight or obese and/or have diabetes, hyperlipidaemia and/or atherosclerosis, or be at risk of developing such a condition. The risk may arise from genetic factors, age, or environmental factors, such as diet.

The patient may have other condition(s) associated with obesity, for example coronary heart disease, stroke, obstructive sleep apnoea, arthritis (for example osteoarthritis) or reduced fertility.

Accordingly, a further aspect of the invention provides the use of a compound of formula I as defined herein in the manufacture of a medicament for the treatment of a patient who is overweight or obese and/or has diabetes, hyperlipidaemia, atherosclerosis, coronary heart disease, stroke, obstructive sleep apnoea, arthritis (for example osteoarthritis) and/or reduced fertility, or is at risk of developing such a condition.

A further aspect of the invention provides the use of a compound of formula I in the manufacture of a medicament for the treatment of a patient in need an antitumour agent or an antiinflammatory agent or of modulation of lipid or eicosanoid status. Preferences in relation to such a patient are noted above.

As is well known to those skilled in the art, obesity may be described as a state of excessive accumulation of body fat. Obesity may be determined by determining the body mass index (BMI) for a patient, and/or by measuring subcutaneous fat deposits in the arm using a "pinch test". The BMI is defined as weight (in kilograms) divided by the square of the height in metres. A BMI of 25-30 is considered as overweight and more than 30 as obese. Preferably, treatment leads to lowering of the BMI to less than about 29 to 31, or to a point at which health risks from being overweight are no longer significant.

It will be appreciated that the treatment of the invention may be used in combination with other treatments for the relevant condition. For example in relation to obesity, the patient may follow a calorie-restricted diet and/or follow a program of physical exercise.

The medicament may comprise more than one (e.g. two) compounds of formula I (such as perfluorinated fatty acids or their derivatives). The medicament may comprise a prodrug, for example a molecule which is converted to a molecule with the required biological activity following administration of the medicament to the patient.

Compounds of formula I may be particularly useful in the treatment of patients with diabetes. For example, the compound may be useful in treating type II diabetes. In type I diabetes, the compounds may be useful as an insulin sensitiser and may therefore allow the dose of insulin administered to be reduced, thereby lowering costs and potentially reducing side effects of insulin administration. Existing anti-diabetic agents, for example the thiazolidinedione class of agents, may have the undesirable effect of stimulating weight gain. Compounds of formula I, such as perfluoroalkyl carboxylic acid compounds and their derivatives (e.g. PFOA or APFO or derivatives thereof), are considered to have the desirable effect of preventing weight gain as well as being useful as anti-diabetic agents.

Compounds of the invention may be useful in the concomitant treatment of a number of abnormalities, for example diabetes, obesity and hyperlipidaemia. Thus, it may be possible to treat a patient with these conditions (which may often occur together) with a single compound or preparation. This may have benefits, for example in relation to patient compliance, the avoidance of drug interactions, ease of formulation and marketing.

It is preferred that the patient is mammalian, most preferably human or, less preferably a domesticated animal, for example an animal kept as a pet or in agriculture, for example horse, cow, cat or dog.

It is preferred that the compound is a compound wherein the plasma insulin levels are modulated (preferably reduced) in a mammal following administration of the compound to the mammal, relative to either preadministration levels or a control mammal which has not been administered the compound. It is particularly preferred that plasma insulin levels are modulated (for example reduced) (for example relative to a control animal) in a male Fischer 344 rat following administration of the compound to the rat, as described in Example 1. It is sufficient for a reduction to be found at any time following first administration of the compound to the mammal (preferably rat), but it is preferred that such reduction is found (ie appears or is still present) at least seven days after first administration of the compound. It is preferred that a reduction of insulin levels of at least 1, 2, 5, 10, 15, 20, 25, 30, 35, 40, 45, 50, 55, 60, 65, 70, 75 or 80% is achieved.

It will be appreciated that the comparative measurements are made on animals at substantially the same stage of feeding, ie at substantially the same time of day or at substantially the same time following ingestion of food.

When the mammal is a rat, it is preferred that plasma insulin levels are modulated (preferably reduced) following administration of the compound at a level of between 30 and 5000 or 3000 ppm of the diet, preferably between about 50 and 500 ppm, still more preferably about 300 ppm. It is preferred that the test is conducted using the methods and conditions described in Example 1. It is preferred that the change in insulin level is not accompanied by any adverse clinical symptoms or change in behaviour/activity of the mammal. Thus, the animals may be observed in relation to standard clinical chemistry analyses, blood pressure and/or dizziness. Thus, it is preferred that insulin levels are modulated (preferably reduced) following administration of an amount of the compound that does not produce a significant adverse effect on the animal.

Tests may be performed on more than one animal for a compound or given dose of a compound, as known to those skilled in the art.

Alternatively or in addition, it is preferred that plasma cholesterol, glucose and/or triglyceride levels are modulated (preferably reduced), and/or leptin levels modulated, in a mammal following administration of the compound to the mammal, relative to either preadministration levels or a control mammal which has not been administered the compound. Preferences indicated above in relation to modulation (for example reduction) of insulin levels apply similarly in relation to modulation (for example reduction) of plasma cholesterol, glucose and triglyceride levels, and to modulation of leptin levels. Alternatively or in addition, eicosanoid status (ie type or concentration) may be modulated (preferably reduced) in a mammal (or in a particular locus or tissue) following administration of the compound to the mammal, relative to either preadministration levels or a control mammal which has not been administered the compound.

Alternatively or in addition, it is preferred that bodyweight or bodyweight gain is modulated (preferably reduced) in a mammal following administration of the compound to the mammal, relative to either preadministration levels (for bodyweight) or a control mammal (for bodyweight or bodyweight gain) which has not been administered the compound. Preferences indicated above in relation to modulation (for example reduction) of insulin levels apply similarly in relation to modulation (for example reductions) in bodyweight or bodyweight gain.

Food consumption (expressed as weight of food consumed per unit bodyweight) may be increased following administration of the compound to the mammal, relative to either preadministration levels or a control mammal which has not been administered the compound. The increase may not be seen immediately after commencing administration of the compound; an initial decrease may be seen, which may be followed by an increase.

Whilst not wishing to be bound by theory, it is considered that a compound of the invention, for example a perfluorinated fatty acid, for example APFO or PFOA, may bind to a peroxisome proliferator activated receptor (PPAR), for example PPARα, PPARδ or PPARγ (Kliewer et al (1994) PNAS, 91, 7355-7359; reviewed in Gelman et al (1999) Cell Mol Life Sci 55, 932-943; Kersten et al (2000) Nature 405, 421-424 and Issemann & Green (1990) Nature 347, 645-650) and may be a PPAR agonist or antagonist. It is preferred that the compound binds to a peroxisome proliferator activated receptor (PPAR), for example PPARα, PPARδ or PPARγ. It is further preferred that the compound is a PPARα, PPARδ or PPARγ modulator, for example a PPARα, PPARδ or PPARγ agonist or antagonist. It is particularly preferred that the compound is a PPARα or PPARγ agonist or a PPARδ antagonist. Any suitable method may be used for determining whether a compound binds to and/or is a modulator, for example an agonist or antagonist of a PPAR.

Also whilst not wishing to be bound by theory, a compound of the invention, for example a perfluorinated fatty acid, for example APFO or PFOA, may bind to a lipid metabolising or binding entity, for example a cycloxygenase, for example COXI or COXII, or phospholipase A, for example Phospholipase A2, or lipoxygenase and may be a modulator, for example an activator or inhibitor, of such an entity's activity (including degree of activation). It is preferred that the compound binds to a lipid metabolising enzyme, for example a cycloxygenase, for example COXI or COXII. It is further preferred that the compound is a modulator of the activity of a lipid metabolising enzyme, for example a cycloxygenase, for example COXI or COXII. Any suitable method may be used for determining whether a compound binds to and/or is a modulator, for example an activator or inhibitor of a lipid binding or metabolising entity.

A further aspect of the invention provides the use of a compound of formula I as defined herein in the manufacture of a medicament for treating a patient in need of modulation of PPAR (for example PPARα, PPARδ (also known as β) or PPARγ) activity. Preferably the patient is in need of an increase in PPAR (preferably PPARα and/or PPARγ) activity and the compound of formula I as defined herein is a PPAR (for example a PPARα or γ) agonist. Alternatively, the patient is in need of a decrease in PPAR (preferably PPARδ) activity and the compound of formula I as defined herein is a PPAR (for example a PPARδ) antagonist.

A further aspect of the invention provides the use of a compound of formula I as defined herein in the manufacture of a medicament for treating a patient in need of modulation of a lipid metabolising entity activity, for example cycloxygenase (for example cyclooxygenase I or cyclooxygenase II) activity or phospholipase A (for example phospholipase A2) activity or lipoxygenase activity.

A further aspect of the invention provides a screening method for identifying a drug-like compound or lead compound for the development of a drug-like compound in which (1) a mammal is exposed to a compound of formula I as defined herein (for example a perfluorinated fatty acid) or derivative thereof (2) the plasma insulin, glucose, cholesterol, triglyceride and/or leptin level of the mammal is measured, and/or bodyweight of the mammal is measured, and/or lipid or eicosanoid status (ie type and level of at least one lipid or eicosanoid) or function (for example assessed by degree of responsiveness to the mammal to a lipid or eicosanoid) of the mammal is measured.

The method preferably comprises the step of selecting a compound on exposure to which the plasma insulin, glucose, cholesterol, and/or triglyceride level of the mammal is changed, preferably reduced, and/or leptin level of the mammal is modulated, and/or bodyweight or bodyweight increase is changed, preferably reduced. Preferences for this aspect of the invention include those indicated above in relation to investigating effects on insulin, cholesterol, glucose, triglyceride or leptin levels, or on bodyweight. For example, it is preferred that the mammal is a rodent, for example a rat or a mouse, or other laboratory animal such as a dog.

A further aspect of the invention provides a screening method for identifying a drug-like compound or lead compound for the development of a drug-like compound in which (1) a mammal is exposed to a compound of formula I as defined herein (for example a perfluorinated fatty acid) or derivative thereof (2) the plasma insulin, glucose, cholesterol, triglyceride and/or leptin level of the mammal is measured, and/or bodyweight of the mammal is measured, and/or lipid or eicosanoid status (ie type and level of at least one lipid or eicosanoid) or function (for example assessed by degree of responsiveness to the mammal to a lipid or eicosanoid) of the mammal is measured.

A further aspect of the invention provides a screening method for identifying a drug-like compound or lead compound for the development of a drug-like compound in which (1) a compound of formula I as defined herein or related compound is exposed to a PPAR polypeptide (2) the binding of the compound to the PPAR polypeptide is measured or the change in the activity of the PPAR polypeptide is measured.

Suitable methods by which binding of the compound to the PPAR polypeptide or effect on activity of the PPAR polypeptide may be measured are described, for example, in U.S. Pat. No. 6,028,109. The method may comprise the step of selecting a compound that binds to the PPAR polypeptide and/or changes its activity, for example nucleic acid binding activity and/or transcription factor activity. It is preferred that the selected compound increases PPARα or PPARγ activity ie acts as a PPARα or PPARγ agonist, or decreases PPARδ activity, ie acts as a PPARδ antagonist.

A further aspect of the invention provides a screening method for identifying a drug-like compound or lead compound for the development of a drug-like compound in which (1) a compound of formula I as defined herein or related compound is exposed to a lipid metabolising or binding entity, for example cycloxygenase (for example cyclooxygenase I or cyclooxygenase II) or phospholipase A (for example phospholipase A2) (2) the binding of the compound to the lipid metabolising or binding entity is measured or the change in the activity of the lipid metabolising or binding entity is measured. Suitable methods by which binding of the compound to the lipid metabolising or binding entity or effect on activity of the lipid metabolising or binding entity may be measured will be well known to those skilled in the art. Methods similar to those described in, for example, U.S. Pat. No. 6,028,109, may be suitable, as noted above. The method may comprise the step of selecting a compound that binds to the lipid metabolising or binding entity and/or changes its activity, for example production of arachidonic acid from appropriate phospholipid (phospholipase A) or production of prostaglandin from arachidonic acid (cyclooxygenase). It is preferred that the selected compound decreases the enzymic or binding activity ie acts as an inhibitor of the enzyme or binding entity.

A screening method of the invention may involve comparing the effect achieved using the test compound with that achieved using APFO or PFOA or other compound with desirable properties, as indicated above. A screening method of the invention may involve determining whether the test compound is able to compete with APFO or PFOA or other compound with desirable properties, as indicated above, for example whether it competes with APFO or PFOA for binding to a PPAR polypeptide, for example PPARα, or other lipid metabolising or binding entity, for example COXI, COXII or phospholipase A2.

Useful screening methods (for example in which the effect of the test compound is compared with that of APFO or PFOA or other compound with desirable properties, as indicated above) also include lipid displacement assays, cell (for example adipocyte) differentiation assays, or other phenotypic assays, insulin sensitisation assays, antiinflammatory screen, or investigation of effects on eicosanoid biosynthesis. The compound may be tested in animal models useful in investigating conditions of interest as noted above, such as obesity, diabetes, hyperlipidaemia or carcinogenesis. Such models include obese (ob/ob) or diabetic (db/db) mice, APC/min mice, BB rat or human tumour xenograft models, as known to those skilled in the art.

A further aspect of the invention provides a screening method for identifying a drug-like compound or lead compound for the development of a drug-like compound in which (1) a cell is exposed to a compound of formula I as defined herein (for example a perfluorinated fatty acid) or derivative thereof (2) the phenotype (for example differentiation) and/or eicosanoid biosynthesis of the cell is measured. The method preferably comprises the step of selecting a compound on exposure to which the phenotype, for example differentiation, of the cell is changed, and/or eicosanoid biosynthesis of the cell is changed, preferably reduced.

The screening methods may be useful in identifying a drug-like compound or lead compound for the development of a drug-like compound for treating diabetes, obesity, hypercholesterolaemia and/or hyperlipidaemia.

The methods may further comprise the step of determining whether the compound is toxic or carcinogenic, for example at a concentration sufficient to elicit a change in bodyweight or bodyweight gain, plasma insulin, glucose, cholesterol, triglyceride and/or leptin levels. Such methods will be well known to those skilled in the art.

It will be appreciated that the compound may preferably be tested in more than of the screening methods of the invention. For example, a compound may be tested for its effect on a PPAR polypeptide, and for its effect on a mammal to which it is administered. The toxicity or carcinogenicity of the compound may also be determined.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons molecular weight. A drug-like compound may additionally exhibit features of selective interaction with a particular protein or proteins and be bioavailable and/or able to penetrate cellular membranes, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, difficult to synthesise or has poor bioavailability) may provide a starting-point for the design of other compounds that may have more desirable characteristics.

These "lead" compounds may then be developed further, for example by molecular modelling/and or experiments to determine a structure activity relationship, in order to develop more efficacious compounds, for example by improving potency, selectivity/specificity and pharmacokinetic properties.

The methods may be performed in vitro, either in intact cells or tissues (for example liver cells or adipocytes), with broken cell or tissue preparations or at least partially purified components. Alternatively, they may be performed in vivo. The cells tissues or organisms in/on which the use or methods are performed may be transgenic. In particular they may be transgenic for a PPAR polypeptide or lipid metabolising or binding entity.

It will be appreciated that the polynucleotide encoding the PPAR (for example PPARα, β or γ) or lipid metabolising or binding entity may be mutated in order to encode a variant of the PPAR, for example by insertion, deletion, substitution, truncation or fusion, as known to those skilled in the art. It is preferred that the PPAR or lipid metabolising or binding entity is not mutated in a way that may materially affect its biological behaviour, for example its nucleic acid binding or transcription factor activity or lipid metabolising or binding activity, as appropriate.

The following references relate to the sequences and tissue distribution of PPARs: Auboeuf et al (1997) *Diabetes* 46(8), 1319-1327; Braissant et al (1996) *Endocrinol* 137(1), 354-

366; Mukherjee et al (1994) *J Steroid Biochem Mol Biol* 51, 157-166; Mukerjee et al (1997) *J Biol Chem* 272, 8071-8076.

The following references and GenBank Accession numbers relate to the sequences and/or tissue distribution of the indicated polypeptides.

U63846 Human COX-1 cDNA (PTSG1); Hla (1996) *Prostaglandins* 51, 81-85.

NM000963 Human COX2 cDNA (PTSG2); Hla & Neilson (1992) *PNAS* 89(16), 7384-7388; Jones et al (1993) *J Biol Chem* 268(12), 9049-9054; Appleby et al (1994) *Biochem J* 302, 723-727; Kosaka et al (1994) *Eur J Biochem* 221(3), 889-897.

AF306566 Human phospholipase A2 (secreted form); Valentin et al (2000) *Biochem Biophys Res Commun* 279(1), 223-228.

NM021628 Human lipogenase ALOXE3.

XM005818 Human lipoxygenase ALOXE5.

XM008328 Human lipoxegenase ALOX12.

NM001141 Human lipoxegenase ALOX15; Brash et al (1997) *PNAS* 94(12), 6148-6152.

NM005090 and NM 003706 Human phospholipase A2 (cPLA2-gamma) Underwood et al (1998) *J Biol Chem* 273(34), 21926-21932 and Pickard et al (1999) *J Biol Chem* 274(13), 8823-8831

M68874 Human phospholipase A2 (cPLA2) Sharp et al (1991) *J Biol Chem* 266(23), 14850-14853.

It will be appreciated that such a compound may be an agonist or antagonist of the PPAR polypeptide used in the screen and that the intention of the screen is to identify compounds that act as agonists or antagonists of the PPAR, even if the screen makes use of a binding assay rather than an activity assay, for example transcription factor activity or nucleic acid (for example DNA) binding activity. It will be appreciated that the action of a compound found to bind the PPAR polypeptide may be confirmed by performing an assay of transcription factor activity or nucleic acid binding activity in the presence of the compound.

Likewise, such a compound may be an inhibitor or activator of the lipid metabolising or binding entity used in the screen and that the intention of the screen is to identify compounds that act as inhibitors or activators of the lipid metabolising or binding entity, even if the screen makes use of a binding assay rather than an activity assay, for example lipid metabolising activity, for example prostaglandin production from arachidonic acid for COXI or COXII. It will be appreciated that the action of a compound found to bind the lipid metabolising or binding entity may be confirmed by performing an assay of the appropriate enzyme or binding activity in the presence of the compound.

It is preferred that the assay is capable of being performed in a "high throughput" format. This may require substantial automation of the assay and minimisation of the quantity of a particular reagent or reagents required for each individual assay. A scintillation proximity assay (SPA) based system, as known to those skilled in the art, may be beneficial. Combinatorial chemistry techniques may be used in generating compounds to be tested.

A further aspect of the invention provides a kit of parts of screening system comprising (1) a library of compounds each of formula I as herein defined or a derivative thereof, and (2) a PPAR polypeptide or polynucleotide encoding a PPAR polypeptide, and/or a test mammal. The kit may optionally comprise reagents useful in measuring plasma insulin, glucose, triglyceride and/or cholesterol levels, or in measuring PPAR activity, for example nucleic acid binding. Such reagents will be apparent to those skilled in the art, and may include reagents useful in performing transactivation assays or DNA binding assays.

A further aspect of the invention provides a kit of parts of screening system comprising (1) a library of compounds each of formula I as herein defined or a derivative thereof, and (2) a lipid metabolising or binding entity (for example COXI or COXII or phospholipase A2 or lipoxygenase) or polynucleotide encoding a lipid metabolising or binding entity. The kit may optionally comprise reagents useful in measuring plasma insulin, glucose, triglyceride, cholesterol and/or leptin levels, or in measuring the activity of the lipid metabolising or binding entity, for example a substrate of the lipid metabolising or binding entity (for example arachidonic acid in the case of COXII or lipoxygenase) or reagent useful in measuring a product of a lipid metabolising enzyme, for example in assessing eicosanoid biosynthesis. As well known to those skilled in the art, reagents may include labelled ligand, for example radiolabelled or fluorescently labelled. Direct binding or displacement of ligand may be measured. Binding may be measured using fluorescence resonance energy transfer (FRET) techniques. The kit may optionally include reagents useful in cell differentiation assays, for example adipocyte differentiation assays, as will be known to those skilled in the art.

A further aspect of the invention provides a compound identifiable or identified by a screening method of the invention. A further aspect of the invention provides a compound identified or identifiable by a screening method of the invention for use in medicine. A further aspect of the invention provides a pharmaceutical composition comprising a compound identified or identifiable by a screening method of the invention and a pharmaceutically acceptable excipient. Preferences in relation to properties of such compounds are as indicated above and in relation to the first aspect of the invention.

A compound identified or identifiable by a screening method of the invention is also provided for use in the manufacture of a composition for use as a food supplement or a food additive. The invention also relates to a food product comprising a foodstuff and a compound of formula I as defined herein or a compound identified or identifiable by a screening method of the invention, wherein the food is not laboratory rodent, for example rat or mouse, feed. It is preferred that the food is not laboratory animal feed.

Preferably, the food (the term including food product and foodstuff) is suitable for administration to an animal (for example a domesticated animal as discussed above but not a laboratory rodent) or human, for example an adult human, baby or infant.

A further aspect of the invention provides the use of a compound identified or identifiable by a screening method of the invention in the manufacture of a medicament for the treatment of a patient in need of modulation (for example reduction) of body mass or modulation (preferably reduction or prevention) of increase in body mass, and/or in need of modulation (preferably reduction) of plasma insulin, plasma glucose, plasma triglycerides and/or plasma cholesterol, and/or in need of modulation of plasma leptin. The patient may be obese and/or have diabetes, hyperlipidaemia and/or atherosclerosis, or be at risk of developing such a condition.

A further aspect of the invention provides the use of a compound identified or identifiable by a screening method of the invention in the manufacture of a medicament for the treatment of a patient who is overweight or obese and/or has diabetes, hyperlipidaemia, atherosclerosis, coronary heart disease, stroke, obstructive sleep apnoea, arthritis (for example osteoarthritis) and/or reduced fertility, or is at risk of developing such a condition.

A further aspect of the invention provides the use of compound identified or identifiable by a screening method of the invention in the manufacture of a medicament for treating a patient in need of modulation of PPAR (for example PPARα) or modulation of lipid or eicosanoid status or function, or of lipid metabolising or binding entity (for example COXI, COXII, phospholipase A or lipoxygenase) activity. Preferably the patient is in need of an increase in PPAR (preferably PPARα or PPARγ) activity and the compound is a PPAR (for example a PPARα or PPARγ) agonist. Alternatively, the patient may be in need of a decrease in activity of a lipid metabolising or binding entity and the compound is an inhibitor of that lipid metabolising or binding entity (or entities).

The compounds may be administered in any suitable way, usually parenterally, for example intravenously, intraperitoneally or intravesically, in standard sterile, non-pyrogenic formulations of diluents and carriers. The compounds may also be administered topically. The compounds of the invention may also be administered in a localised manner, for example by injection. Preferably, the compounds are administered orally. The compounds may be administered as a tablet or capsule or as a supplement added to food or drink. A slow-release formulation may be used.

A further aspect of the invention provides a method of treatment of a patient in need of modulation (preferably reduction) of body mass or modulation (for example reduction or prevention) of increase in body mass, and/or in need of modulation (for example reduction) of plasma insulin, plasma glucose, plasma triglycerides, plasma cholesterol and/or leptin, comprising administering to the patient an effective amount of a compound identified or identifiable by the screening method of the invention. A further aspect of the invention provides a method of treatment of a patient who is overweight or obese and/or has diabetes, hyperlipidaemia, atherosclerosis, coronary heart disease, stroke, obstructive sleep apnoea, arthritis (for example osteoarthritis) and/or reduced fertility, or is at risk of developing such a condition, comprising administering to the patient an effective amount of a compound identified or identifiable by the screening method of the invention.

Preferences in relation to the patient and compound are as indicated above.

A further aspect of the invention provides a method of treatment of a patient in need of modulation of PPAR (for example PPARα, δ or γ) activity, or of lipid or eicosanoid status or function, or of a lipid metabolising or binding entity activity, comprising administering to the patient an effective amount of a compound identified or identifiable by the screening method of the invention. Preferably the patient is in need of an increase in PPAR (preferably PPARα or γ) activity and the compound is a PPAR (for example a PPARα or γ) agonist. Further preferences in relation to the patient and compound are as indicated above. Alternatively, the patient may be in need of a decrease in activity of a lipid metabolising or binding entity and the compound is an inhibitor of that lipid metabolising or binding entity or entities.

The invention is now described in more detail by reference to the following, non-limiting, Figures and Examples:

FIG. 1: Growth curves for male Fischer 344 rats administered APFO in diet.

Figure 2:
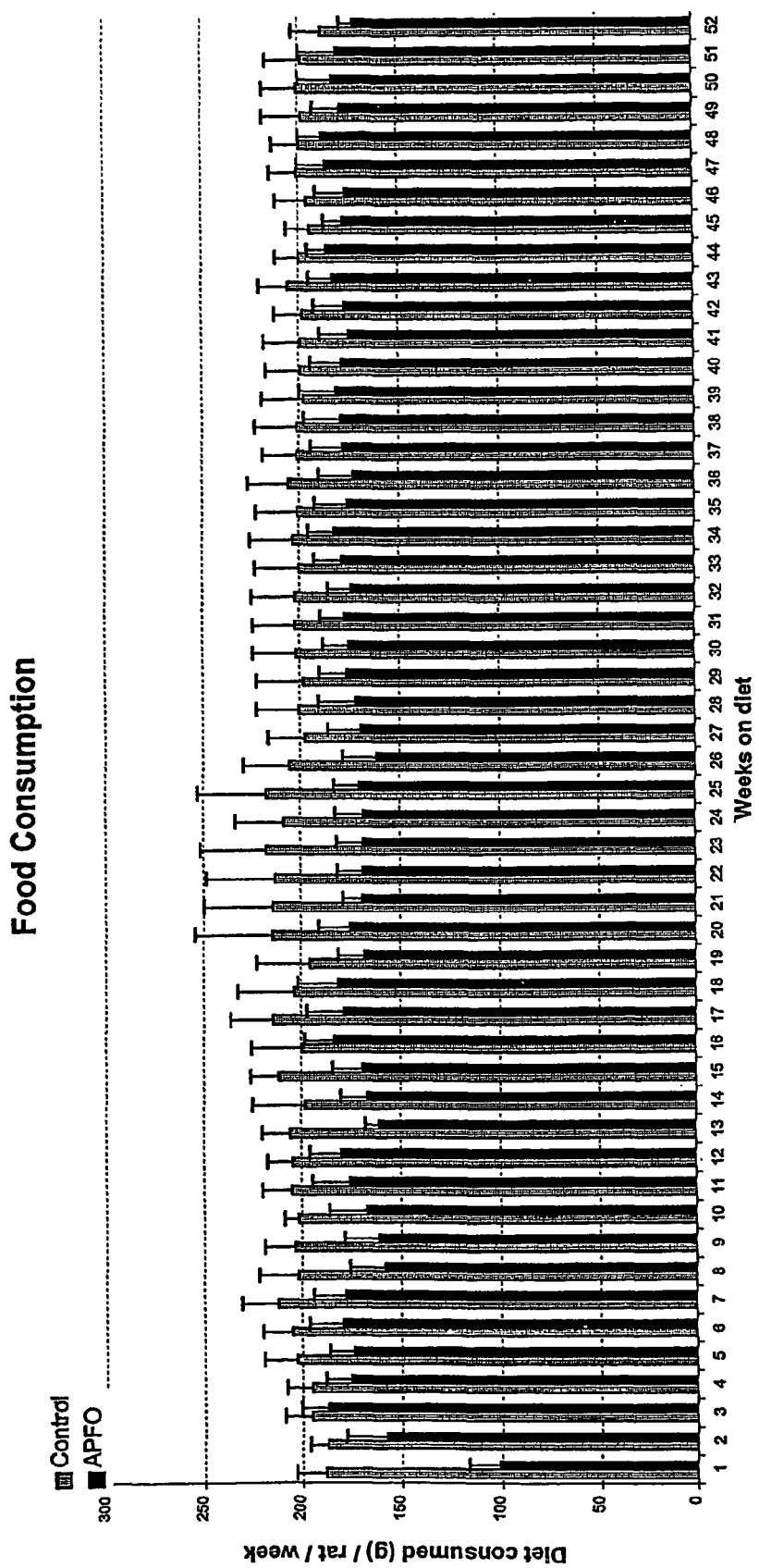

FIG. 2: Food consumption by Fischer 344 rats administered APFO in diet.

Figure 3:
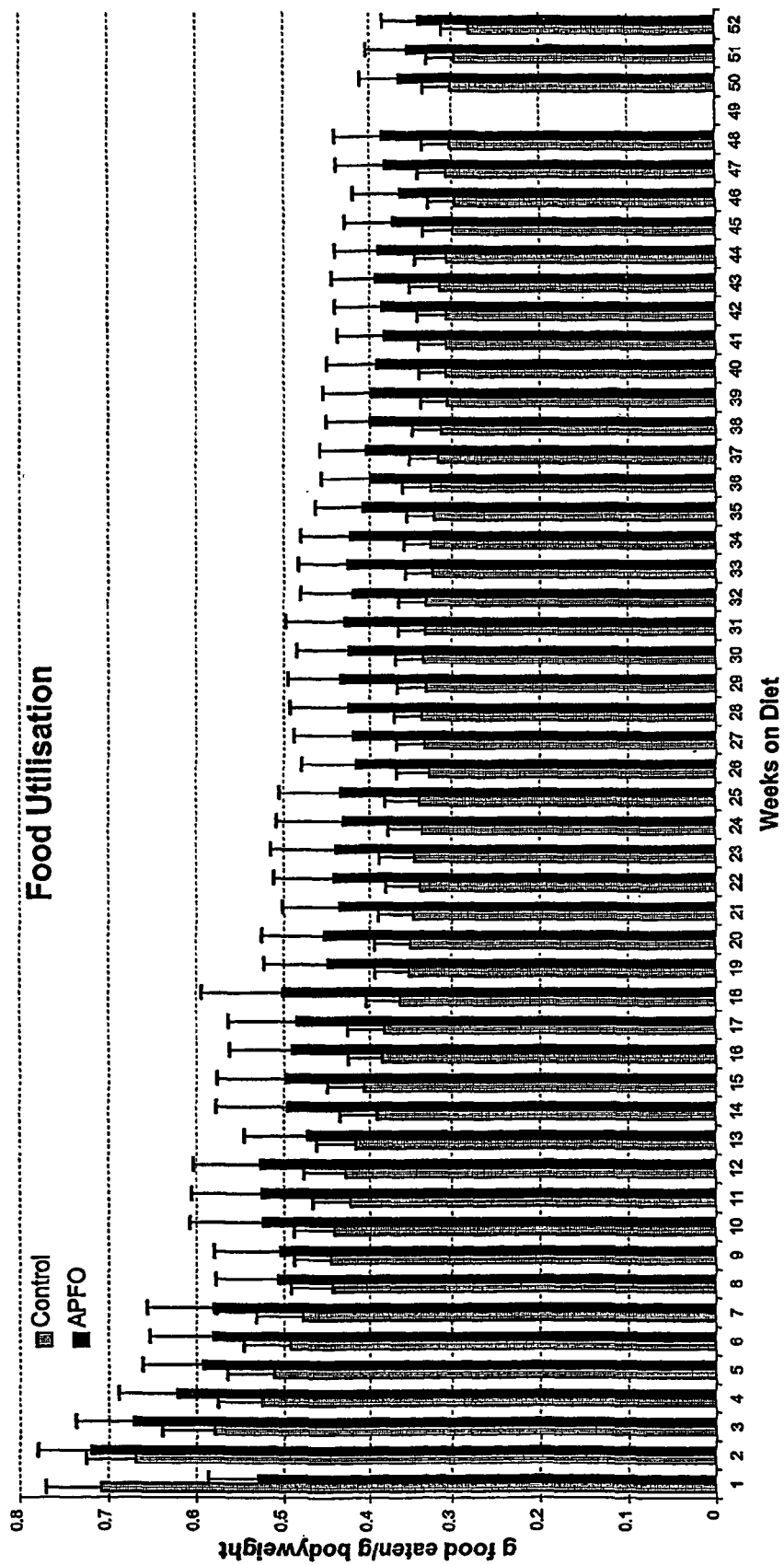

FIG. 3: Food utilisation in Fischer 344 rats administered APFO in diet.

Figure 4:
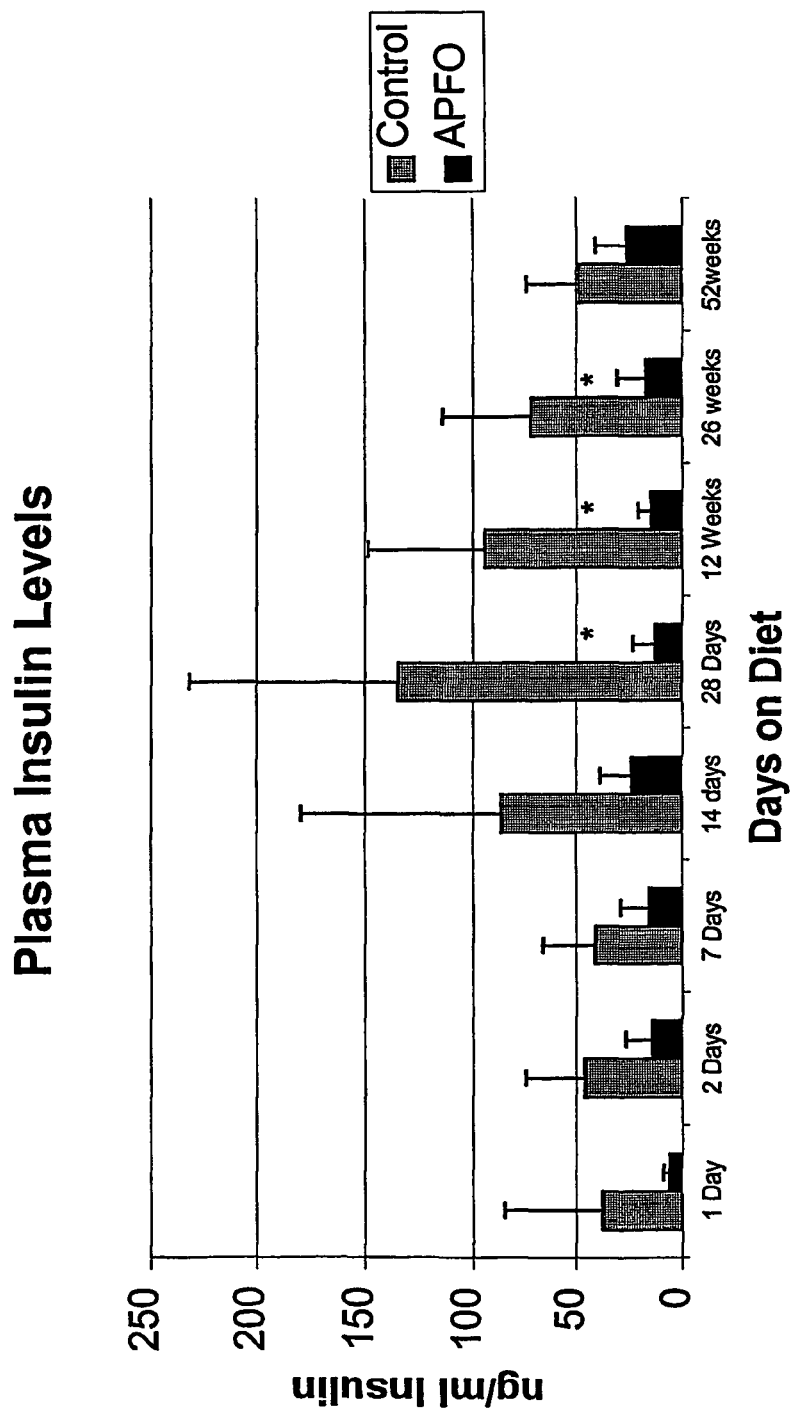

FIG. 4: Effect of APFO treatment on plasma insulin concentration.

Figure 5:
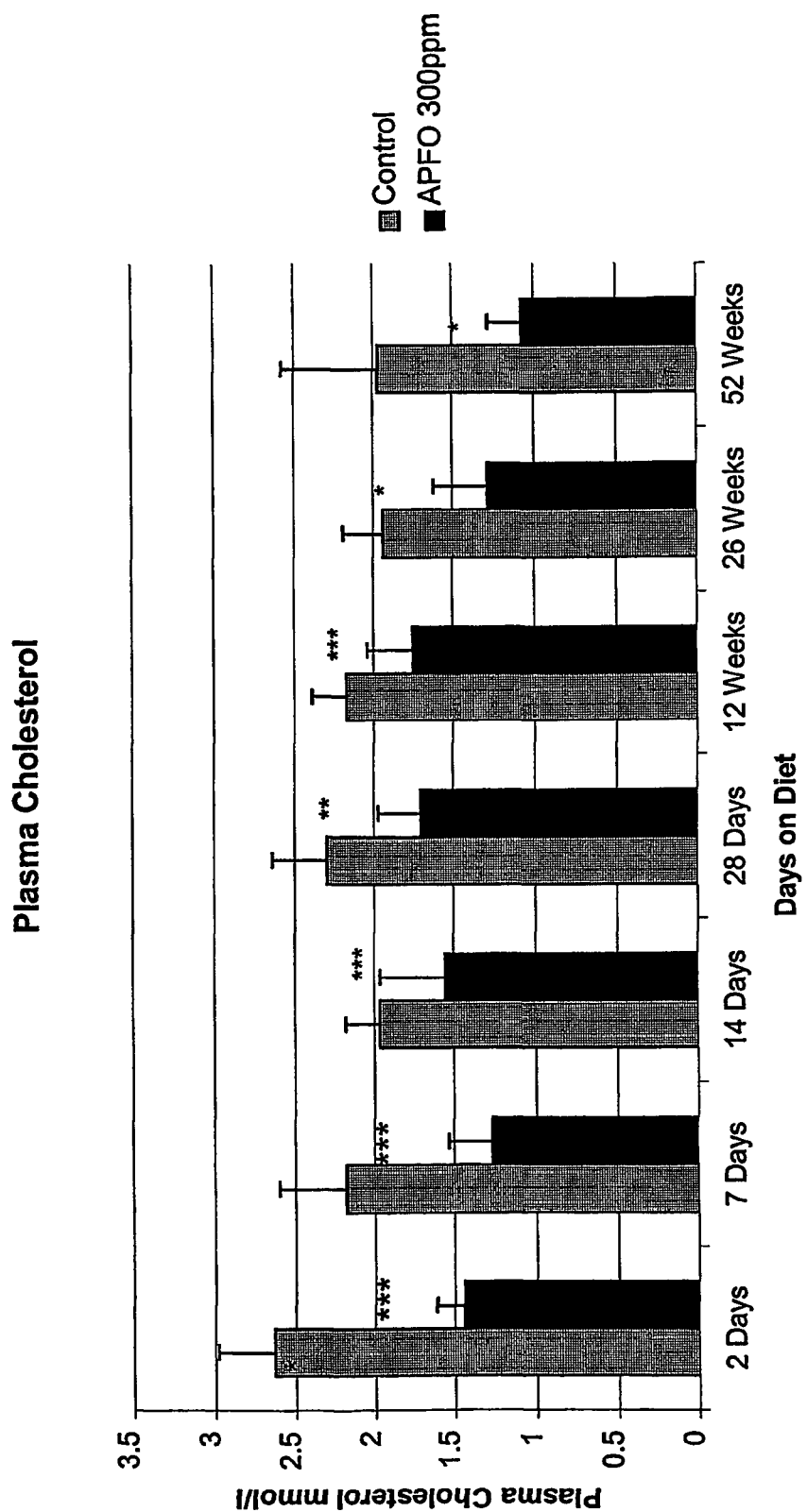

FIG. 5: Effect of APFO on plasma cholesterol concentration.

Figure 6:
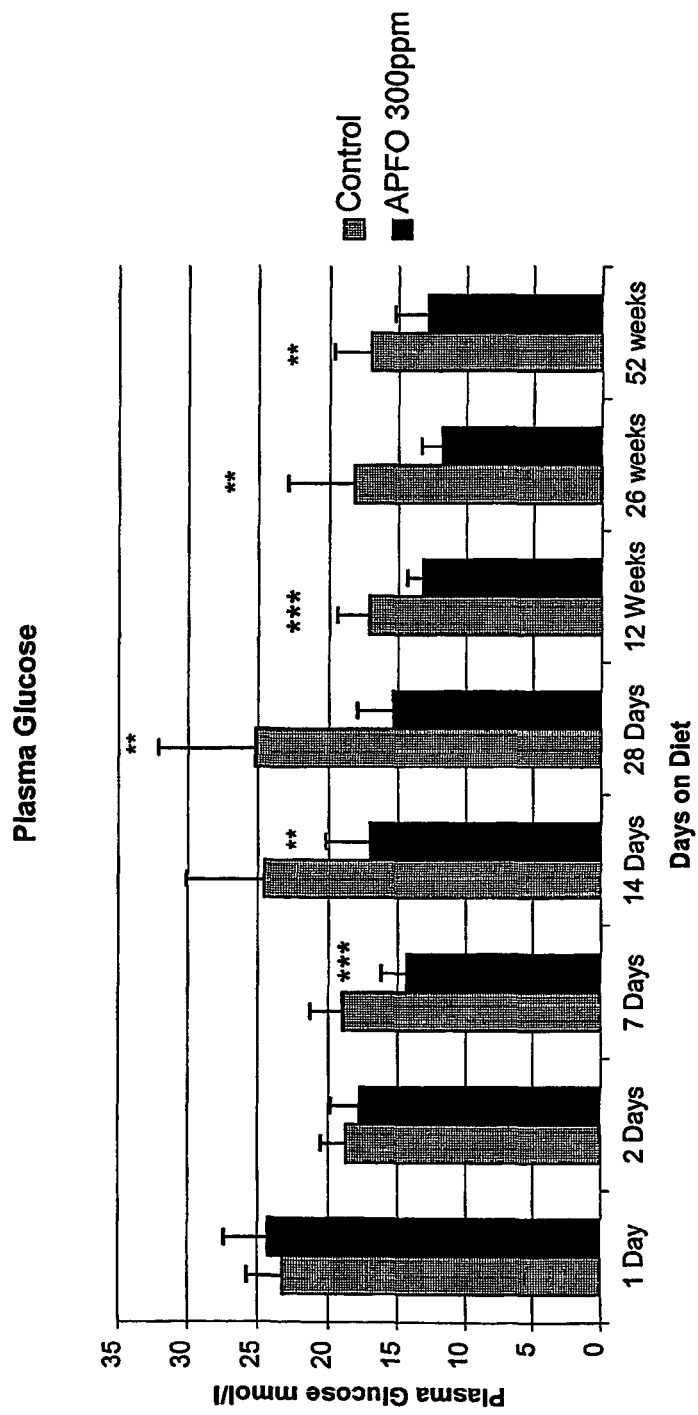

FIG. 6: Effect of APFO on plasma glucose concentration.

Figure 7:
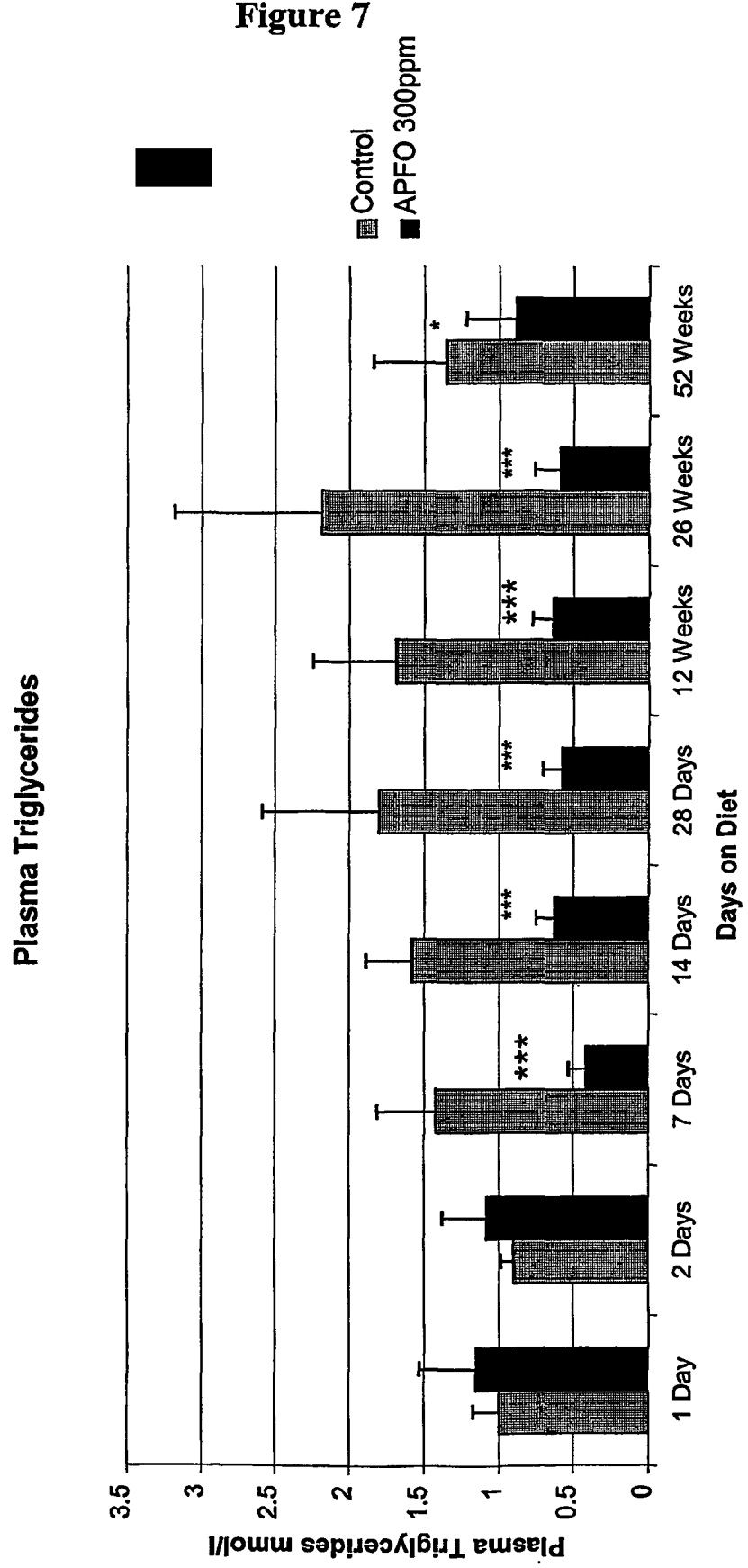

FIG. 7: Effect of APFO on plasma triglyceride concentration.

Figure 8:
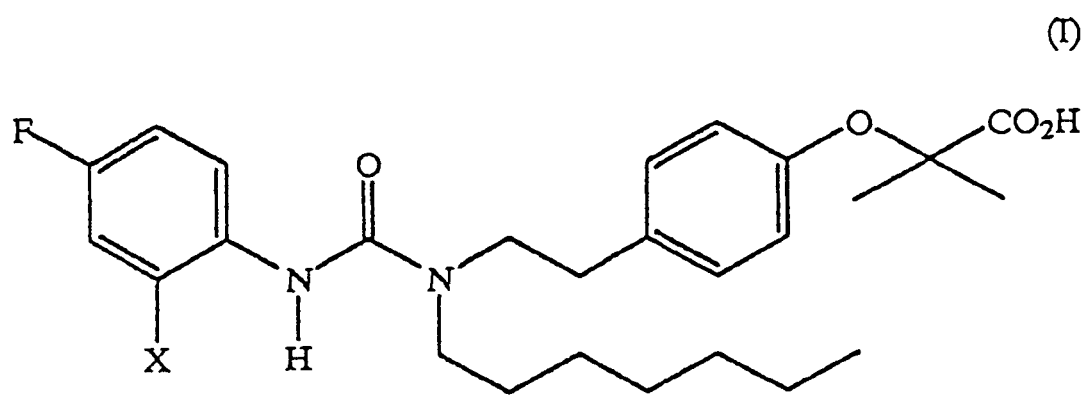

FIG. 8: compounds indicated to be PPAR agonists in U.S. Pat. No. 6,028,109

Figure 9:
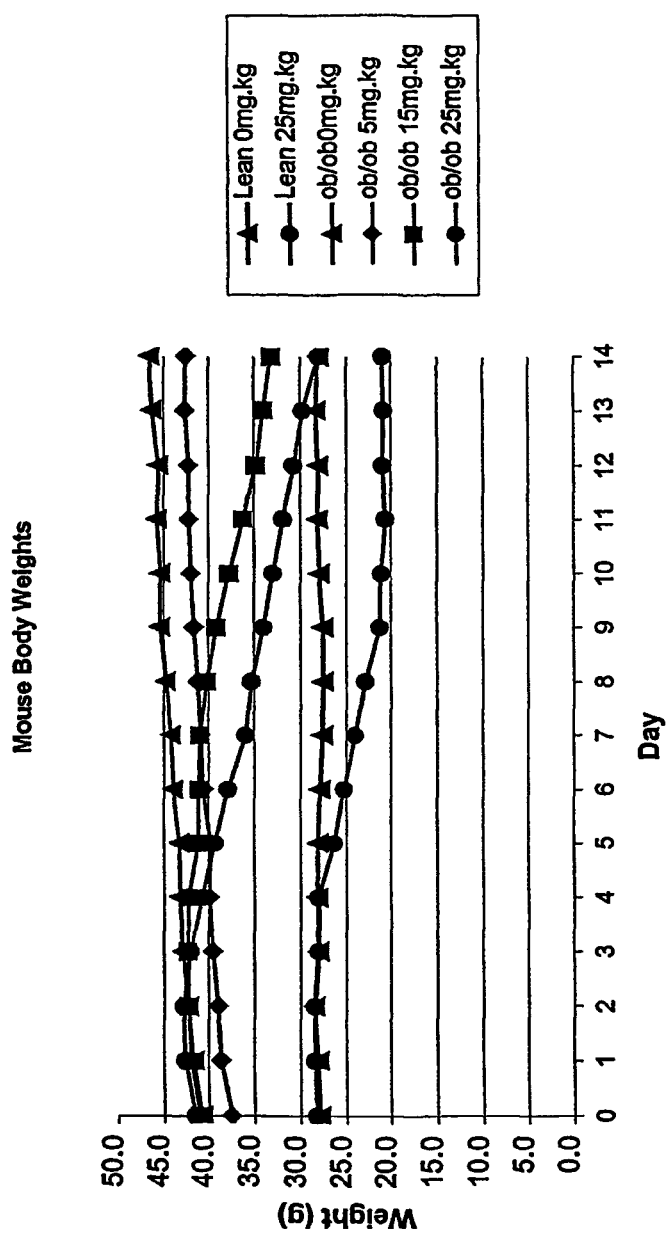

FIG. 9: Effect of APFO treatment on mouse body weights

Figure 10:
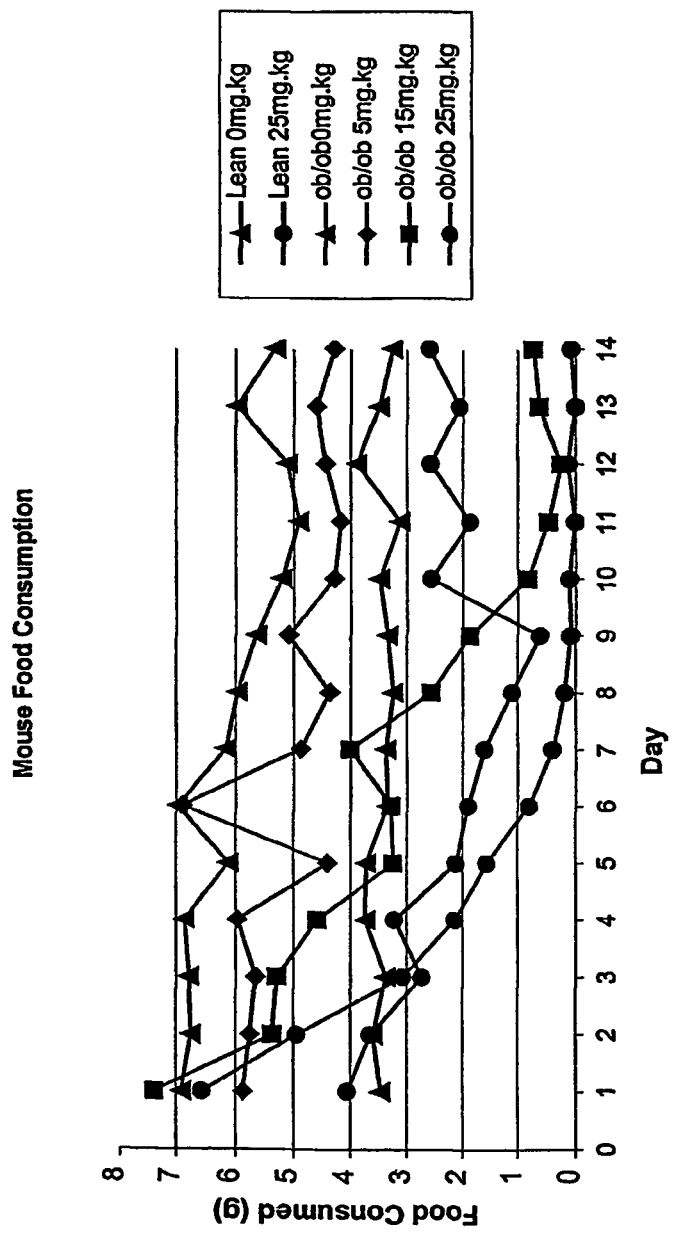

FIG. 10: Effect of APFO treatment on mouse food consumption

Figure 11:
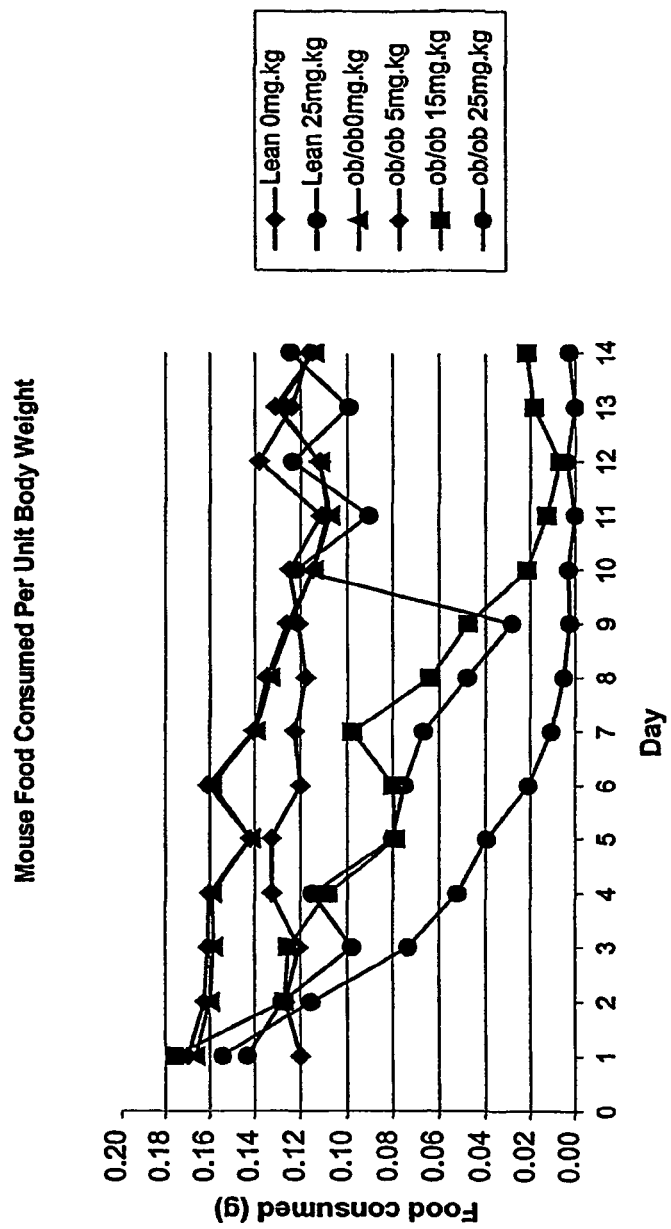

FIG. 11: Effect of APFO treatment on mouse food consumption (expressed as grams food consumed per unit body weight).

Figure 12:
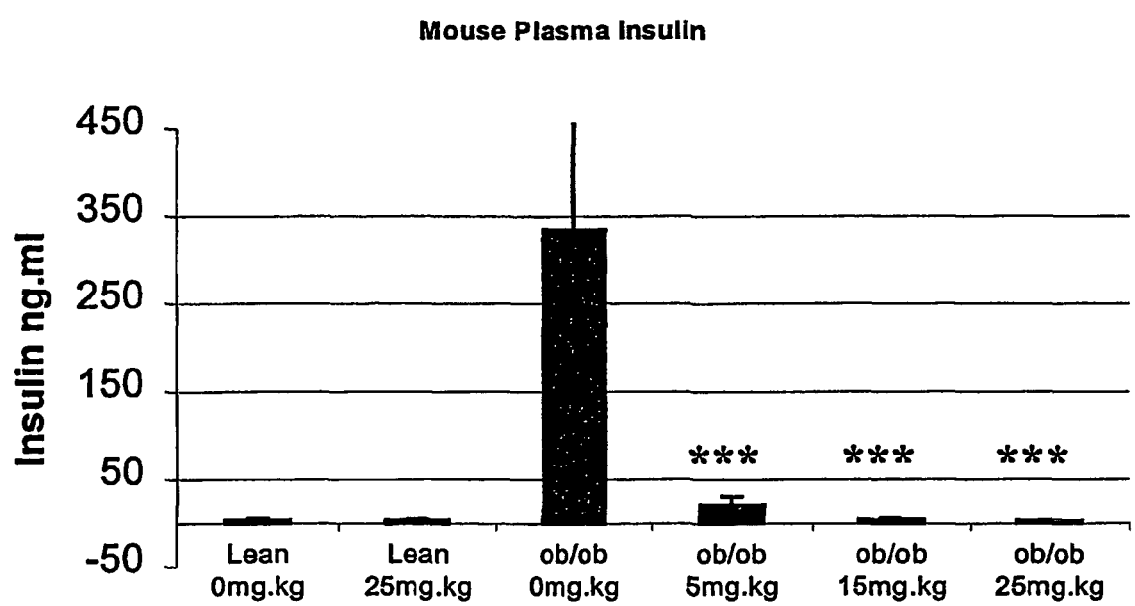

FIG. 12: Effect of APFO treatment on mouse plasma insulin concentration. Values are Mean±SD. Significantly different from respective control group (0 mg/kg); *$p<0.05$; $p<0.01$; *$p<0.001$.

Figure 13:
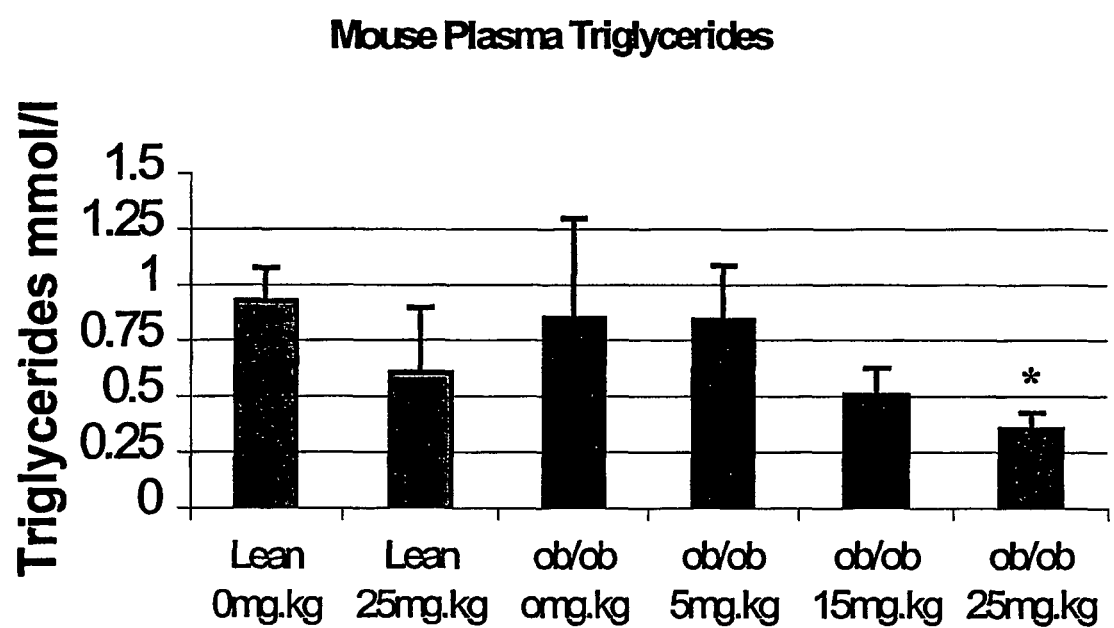

FIG. 13: Effect of APFO treatment on mouse plasma triglyceride concentration. Values are Mean±SD. Significantly different from respective control group (0 mg/kg); *$p<0.05$; $p<0.01$; *$p<0.001$.

Figure 14:
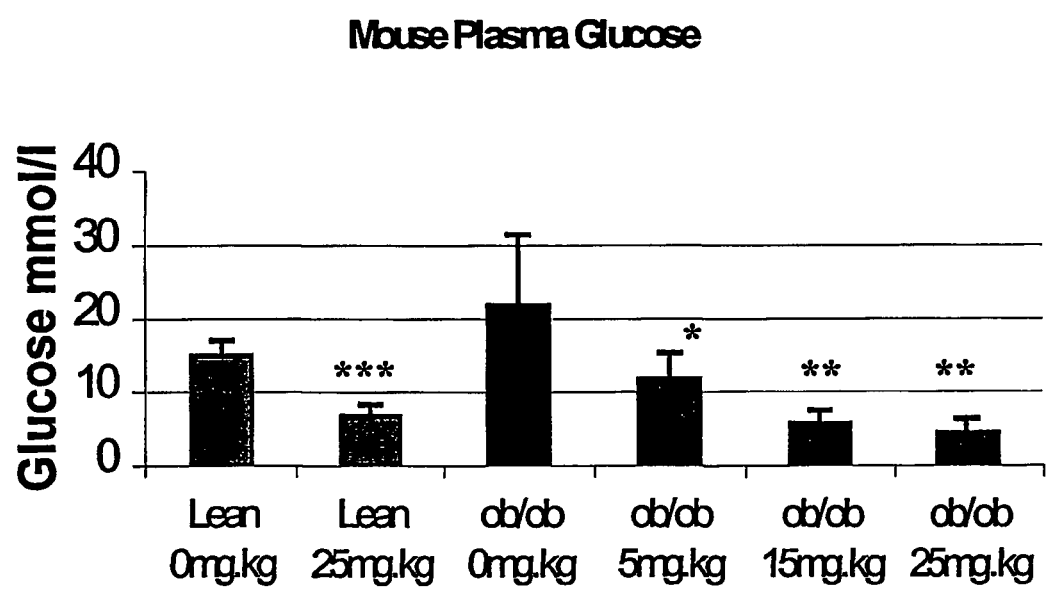

FIG. 14: Effect of APFO on mouse plasma glucose concentration. Values are Mean±SD. Significantly different from respective control group (0 mg/kg); *$p<0.05$; $p<0.01$; *$p<0.001$.

Figure 15:
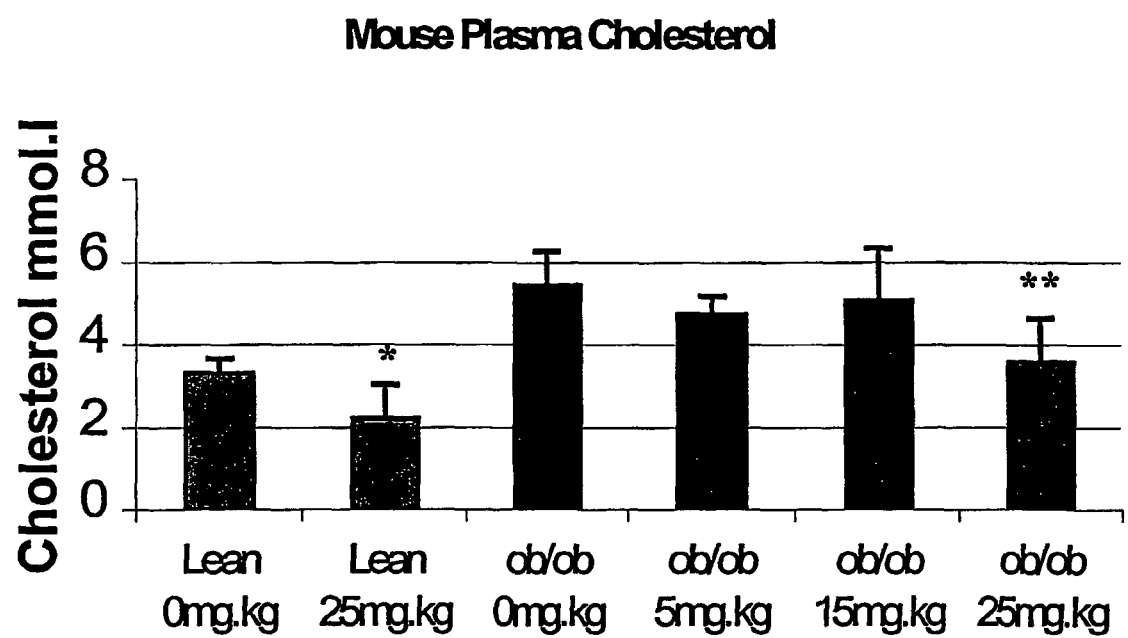

FIG. 15: Effect of APFO treatment on mouse plasma cholesterol. Values are Mean±SD. Significantly different from respective control group (0 mg/kg); *$p<0.05$; $p<0.01$; *$p<0.001$.

Figure 16:
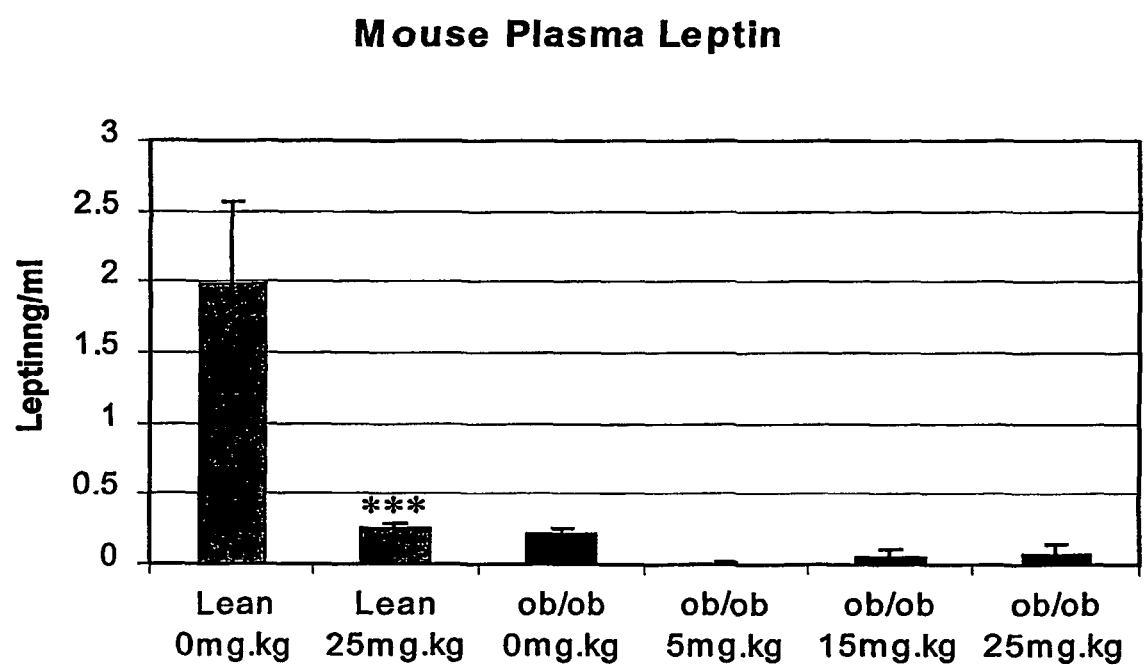

FIG. 16: Effect of APFO treatment on mouse plasma leptin. Values are Mean±SD. Significantly different from respective control group (0 mg/kg); *$p<0.05$; $p<0.01$; *$p<0.001$.

Figure 17:
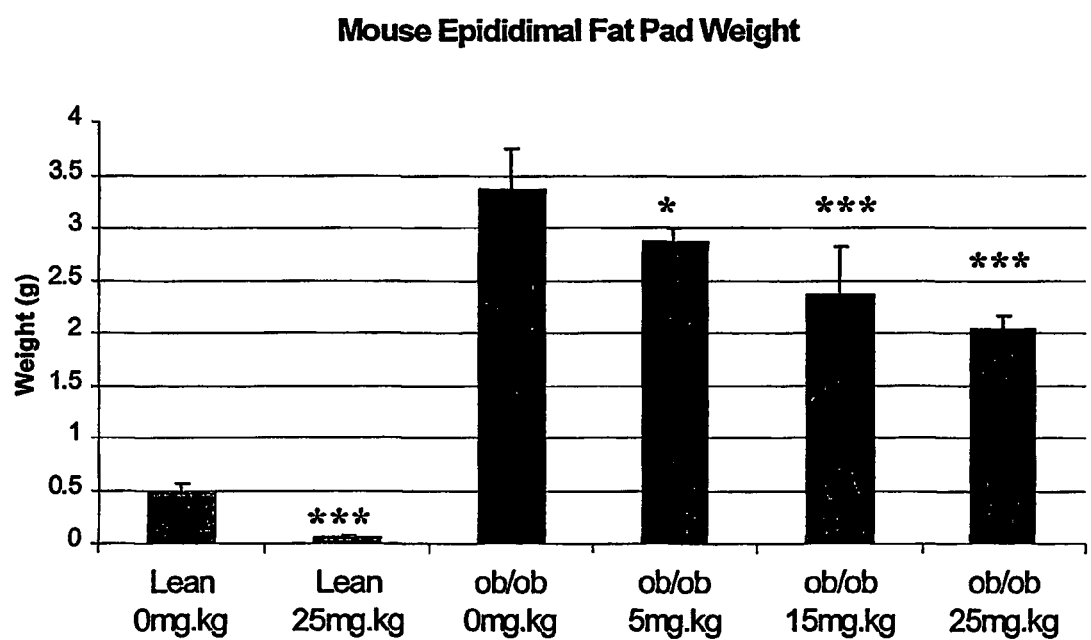

FIG. 17: Effect of APFO treatment of mouse epididimal fat pad weight. Values are Mean±SD. Significantly different from respective control group (0 mg/kg); *$p<0.05$; $p<0.01$; *$p<0.001$.

Figure 18:
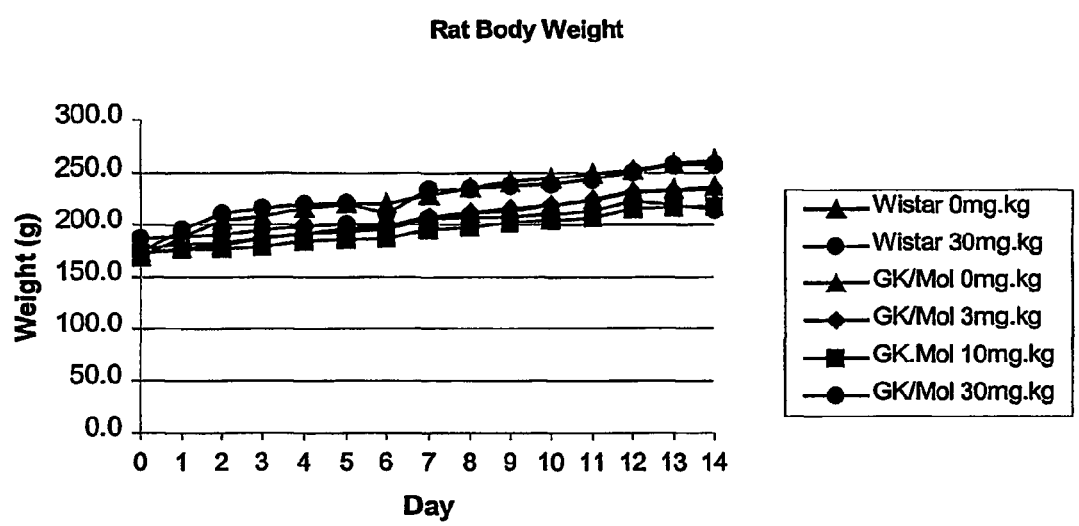

FIG. 18: Effect of APFO treatment on rat body weight.

Figure 19:
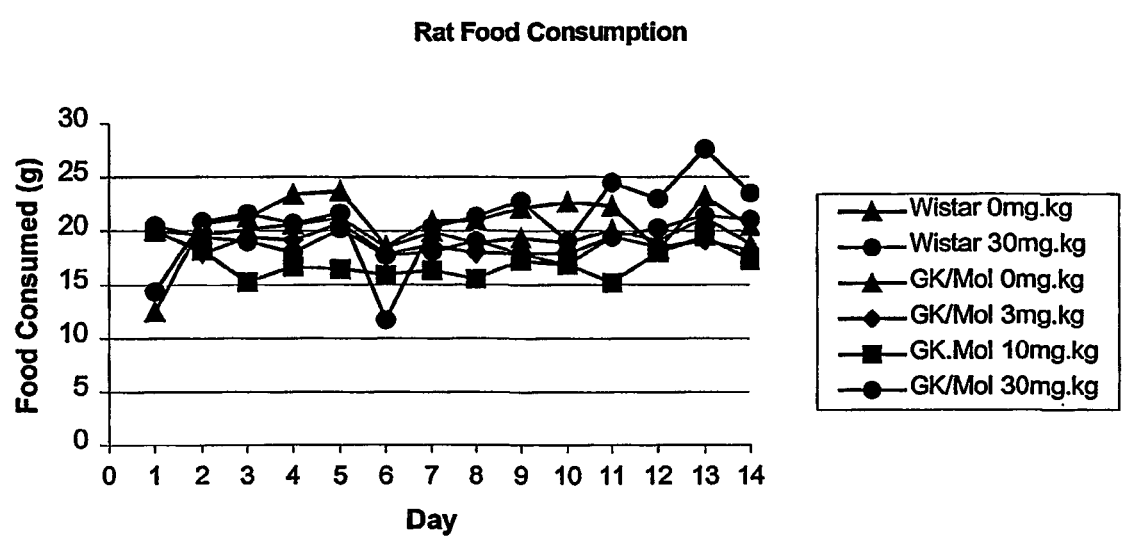

FIG. 19: Effect of APFO treatment on rat food consumption.

Figure 20:
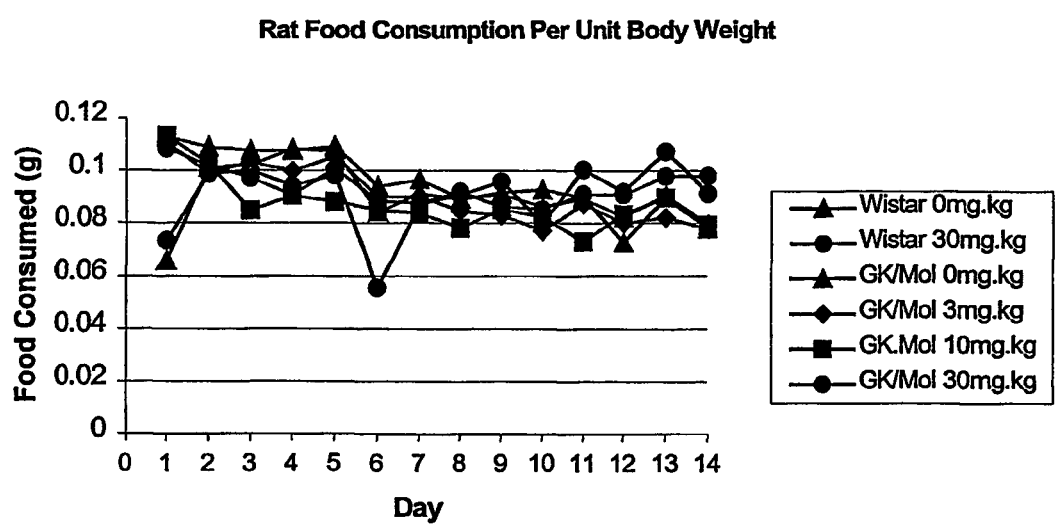

FIG. 20: Effect of APFO on rat food consumption (expressed as grams food consumed per unit body weight).

Figure 21:
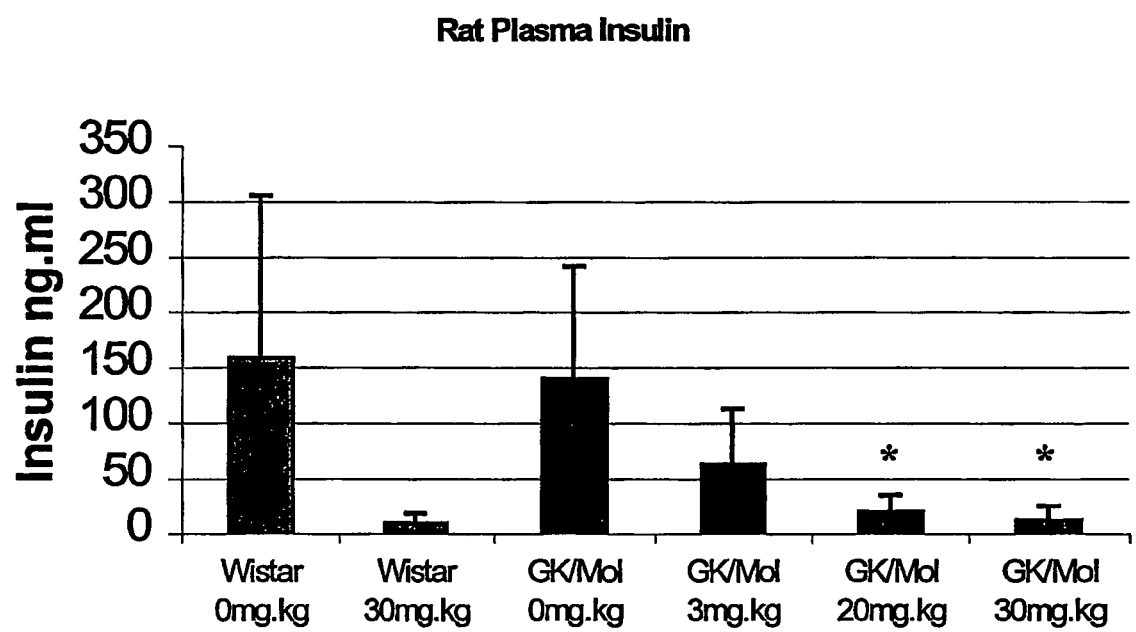

FIG. 21: Effect of APFO treatment on plasma insulin concentration. Values are Mean±SD. Significantly different from respective control group (0 mg/kg); *$p<0.05$; $p<0.01$; *$p<0.001$.

Figure 22:
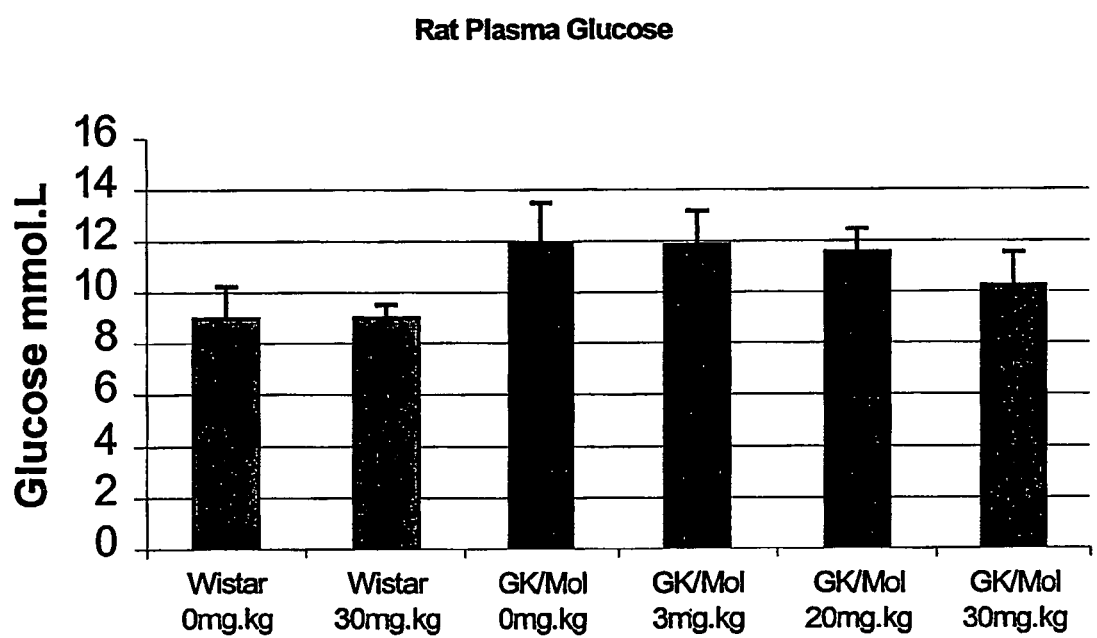

FIG. 22: Effect of APFO treatment on rat plasma glucose concentration. Values are Mean±SD. Significantly different from respective control group (0 mg/kg); *$p<0.05$; $p<0.01$; *$p<0.001$.

Figure 23:
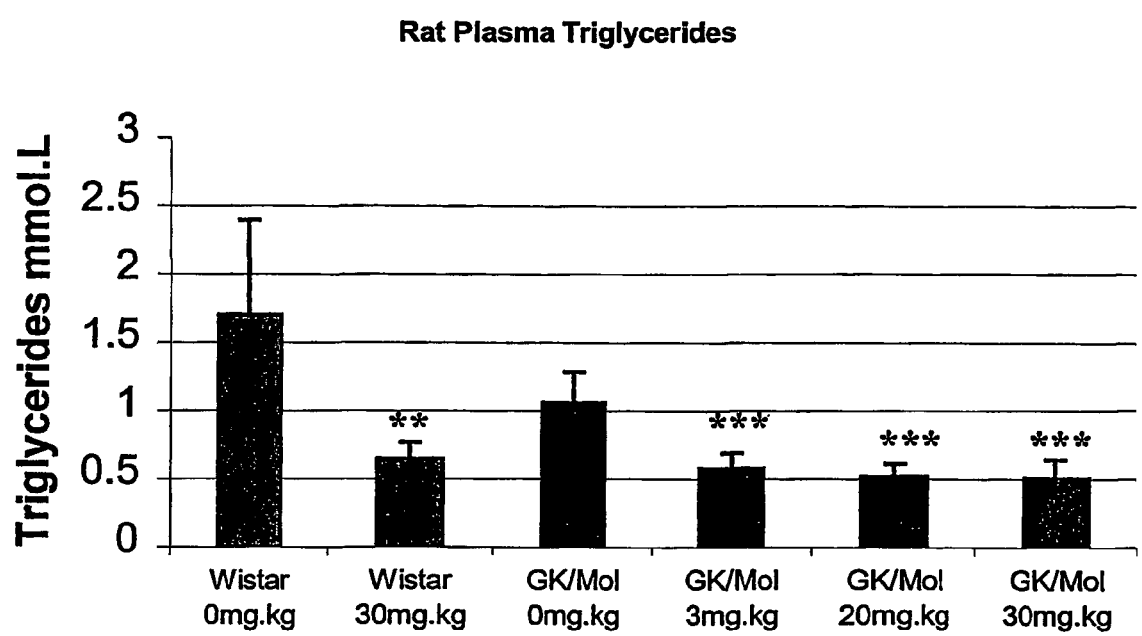

FIG. 23: Effect of APFO treatment on rat plasma triglyceride concentration. Values are Mean±SD. Significantly different from respective control group (0 mg/kg); *$p<0.05$; $p<0.01$; *$p<0.001$.

Figure 24:
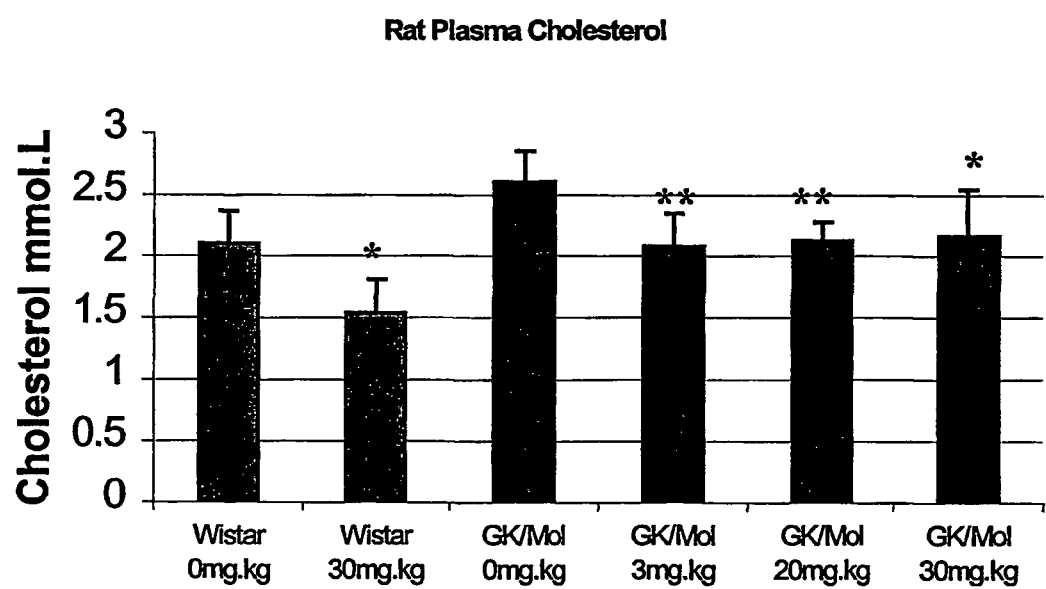

FIG. 24: Effect of APFO treatment on rat plasma cholesterol. Values are Mean±SD. Significantly different from respective control group (0 mg/kg); *$p<0.05$; $p<0.01$; *$p<0.001$.

Figure 25:
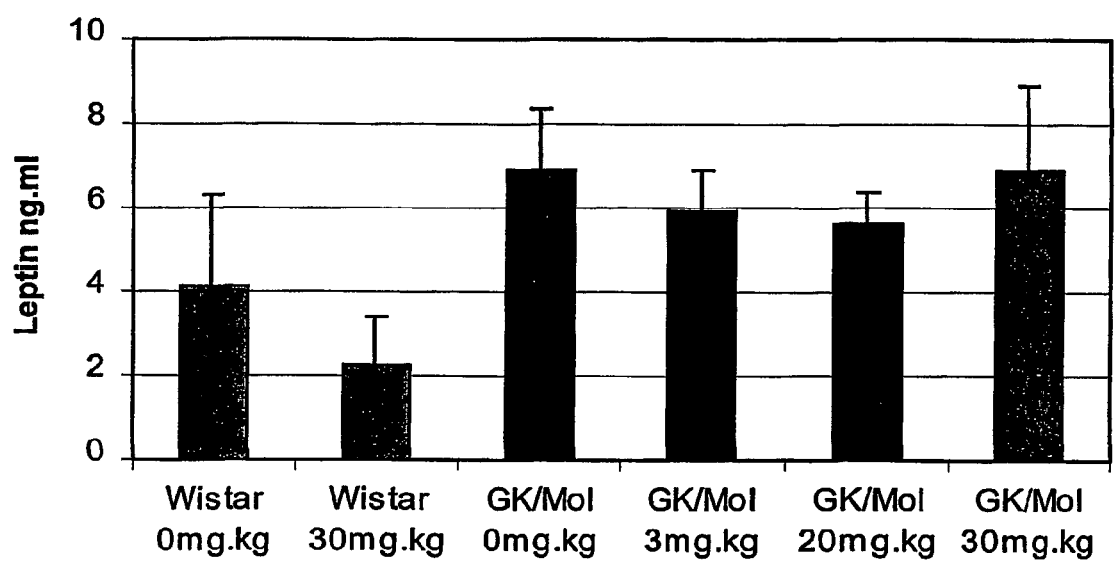

FIG. 25: Effect of APFO treatment on rat plasma leptin concentration.

Figure 26:
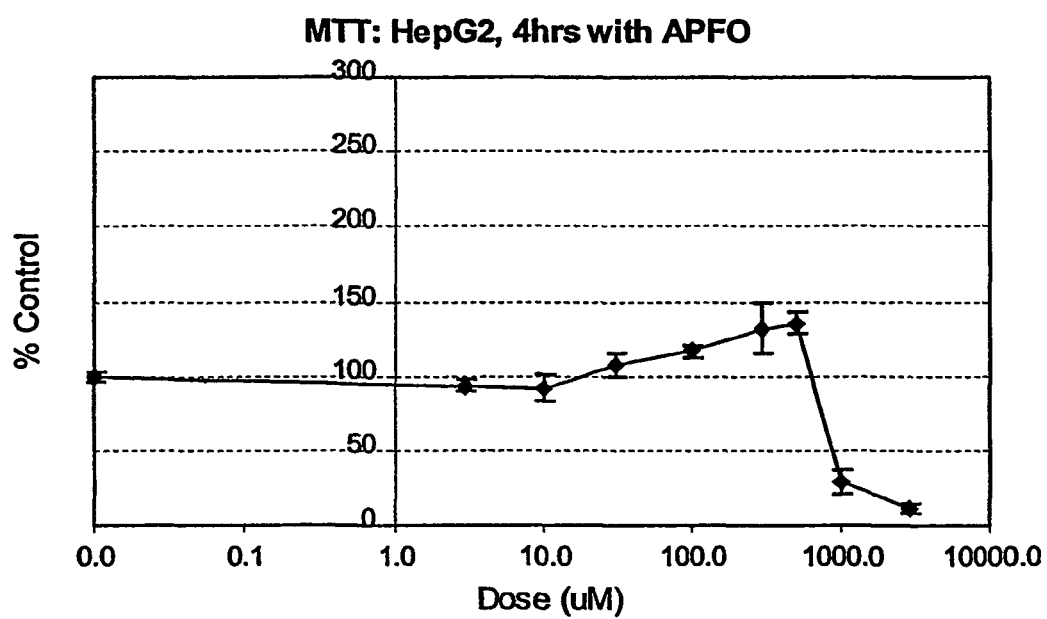
Figure 26:
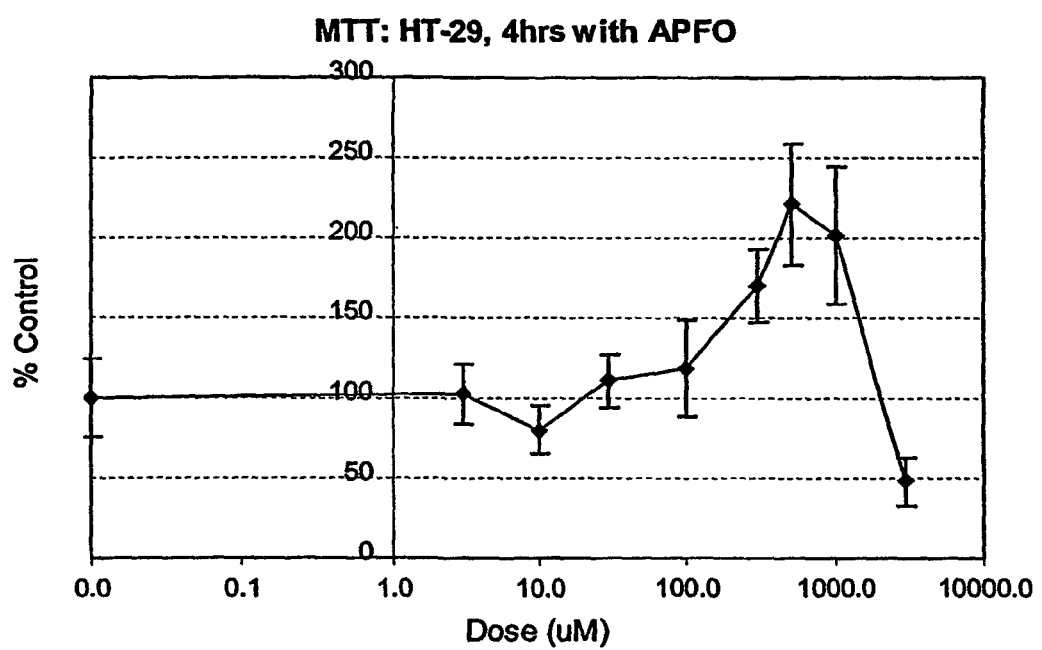
Figure 26:
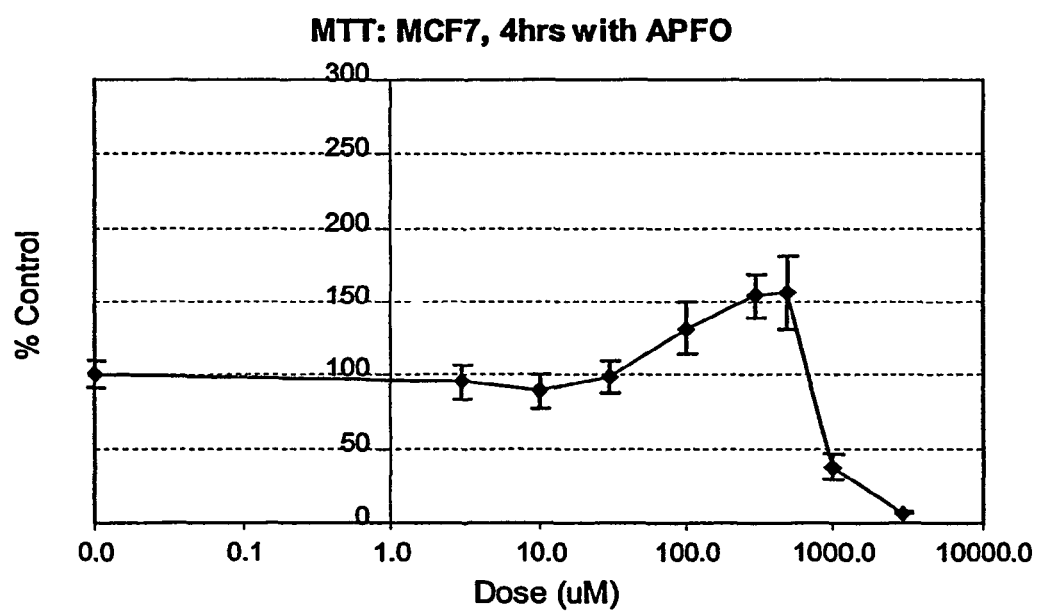

FIG. 26: Cytotoxic effect of APFO on HepG2 cells (A), HT-29 cells (B) and MCF7 cells (C).

Figure 27:
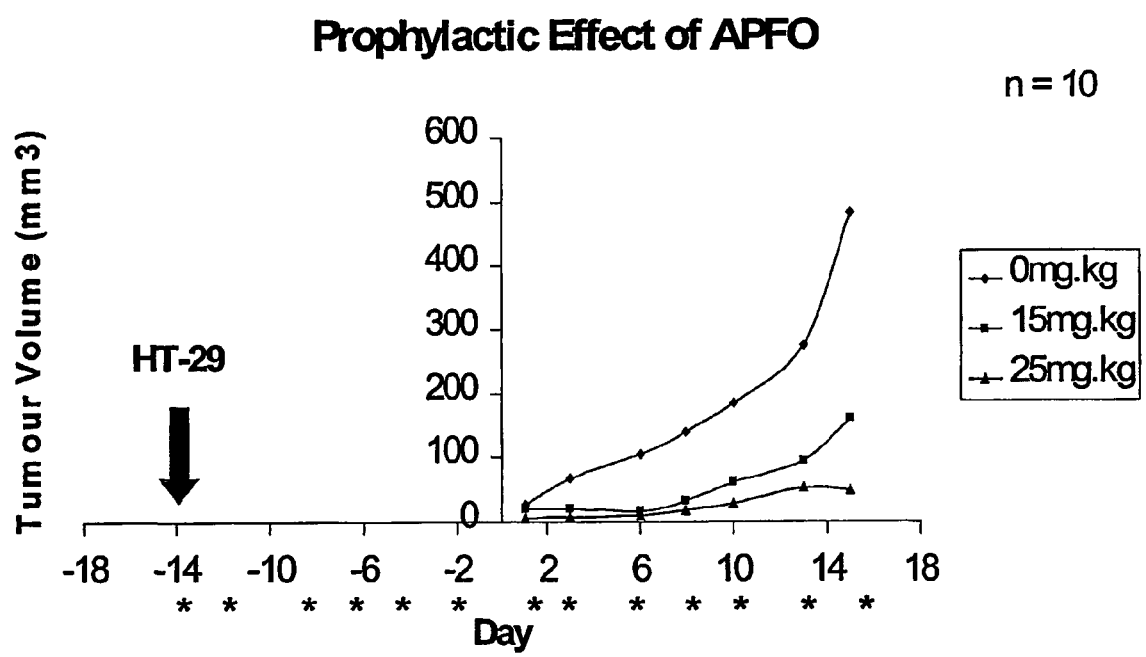

FIG. 27: Effect of prophylactic APFO treatment on tumour volume in an HT-29 xenograft model. *=APFO administration. Arrow indicates the point of tumour cell implantation. Tumour measurement began on day 1.

Figure 28:
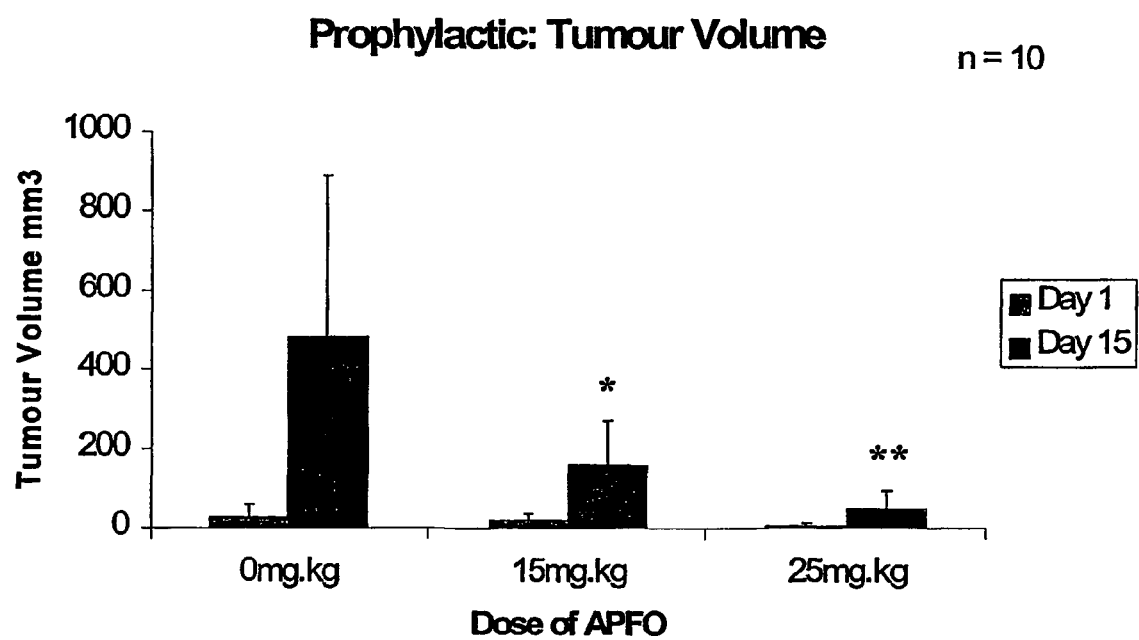

FIG. 28: Effect of prophylactic APFO administration on tumour volume between day 1 and day 15 of treatment. Values are Mean±SD. Significantly different from respective control group (0 mg/kg); *p<0.05; p<0.01; *p<0.001.

Figure 29:
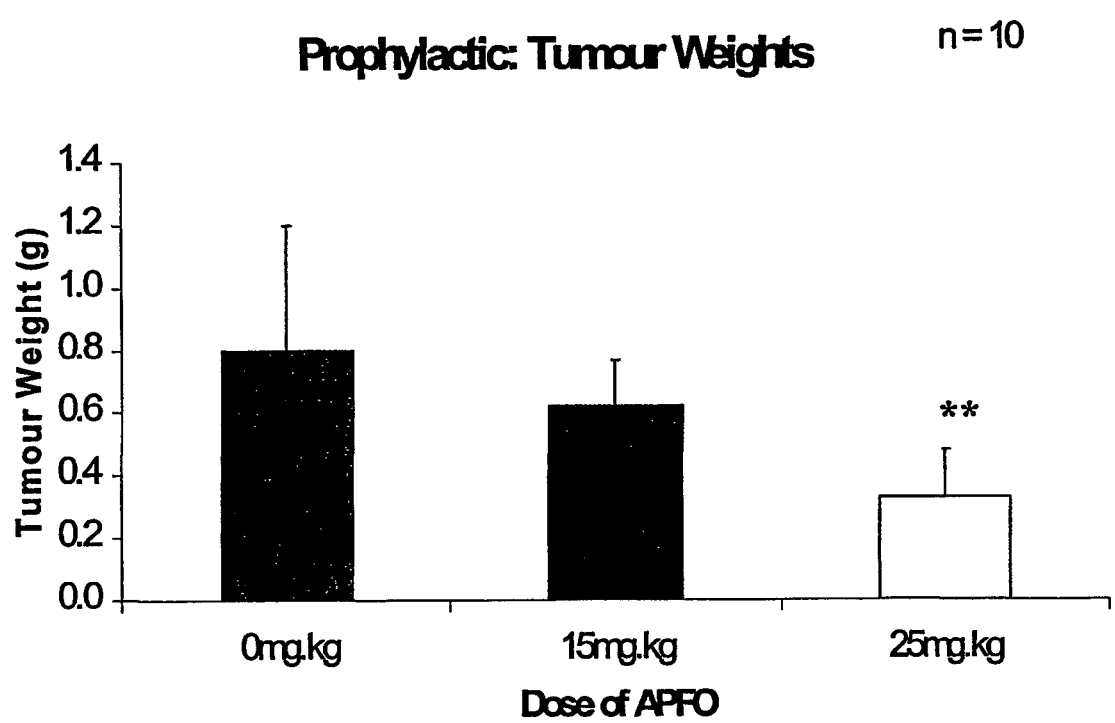

FIG. 29: Effect of prophylactic APFO administration on tumour weight. Values are Mean±SD. Significantly different from respective control group (0 mg/kg); *p<0.05; p<0.01; *p<0.001.

Figure 30:
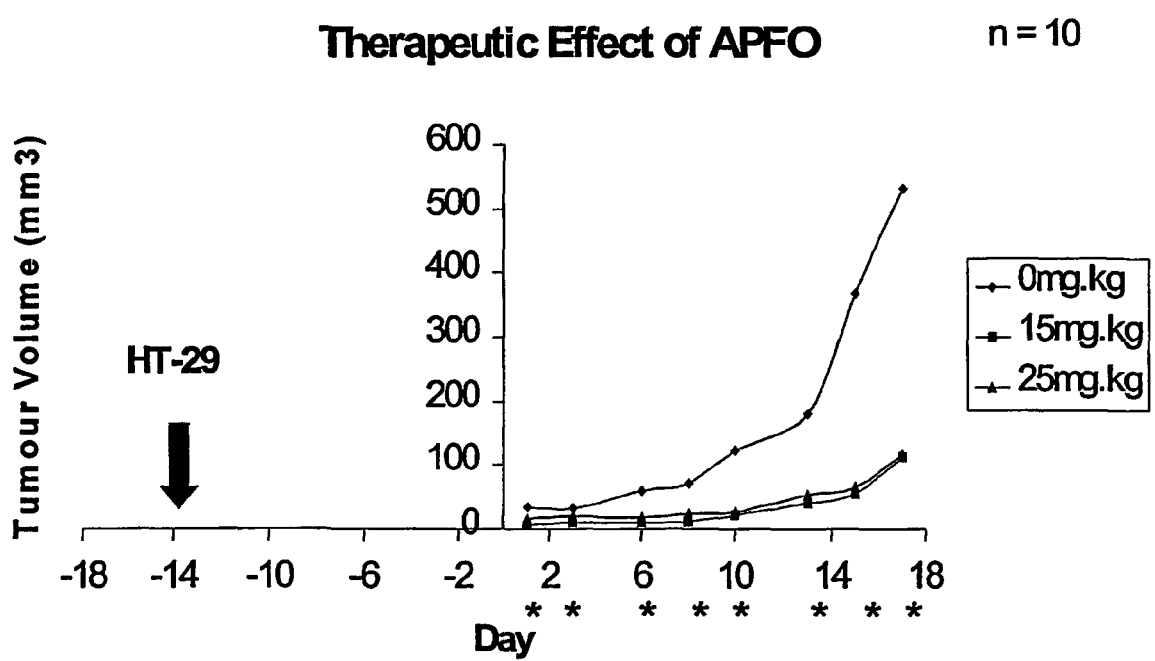

FIG. 30: Effect of therapeutic APFO treatment on tumour volume in an HT-29 xenograft model. *=APFO administration. Arrow indicates the point of tumour cell implantation. Tumour measurement and APFO administration began on day 1.

Figure 31:
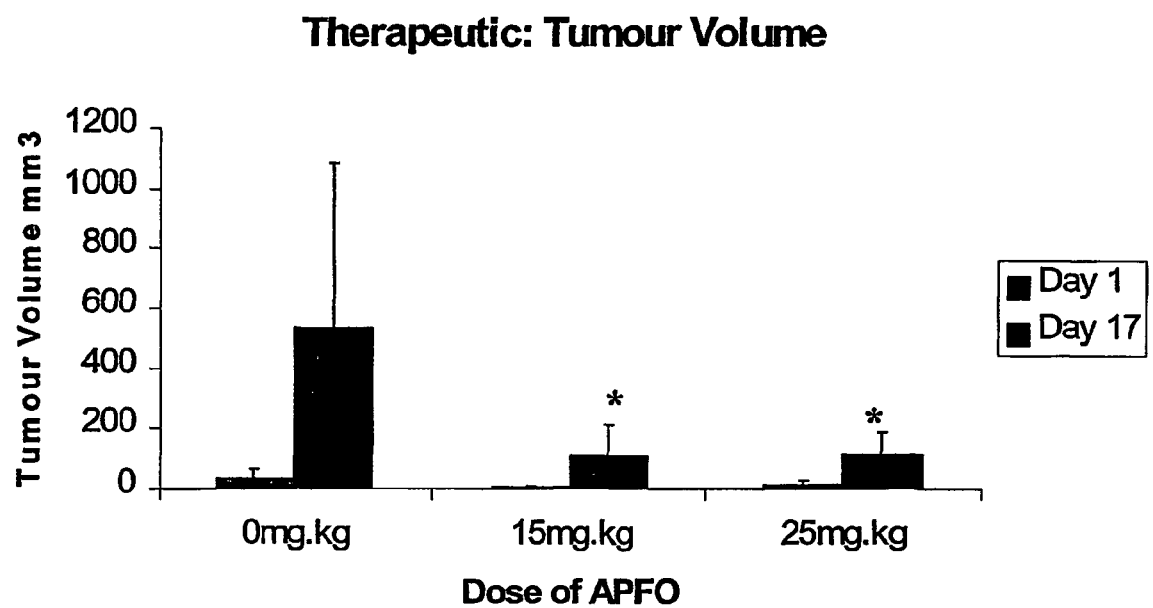

FIG. 31: Effect of therapeutic APPO administration on tumour volume between day 1 and day 17 of treatment. Values are Mean±SD. Significantly different from respective control group (0 mg/kg); *p<0.05; p<0.01; *p<0.001.

Figure 32:
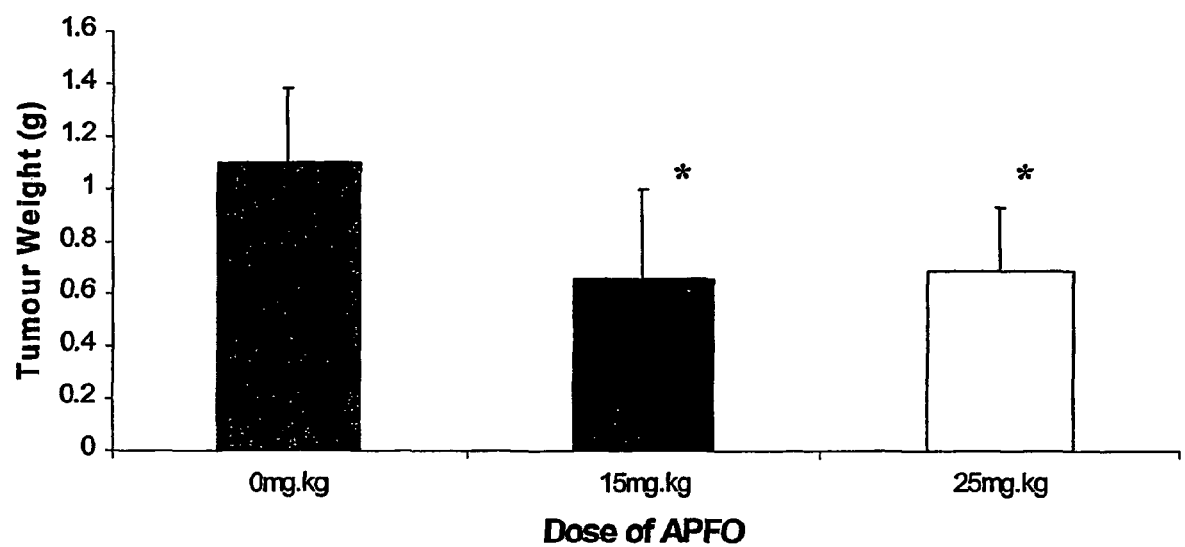

FIG. 32: Effect of therapeutic APFO administration on tumour weight. Values are Mean±SD. Significantly different from respective control group (0 mg/kg); *p<0.05; p<0.01; *p<0.001.

Figure 33:
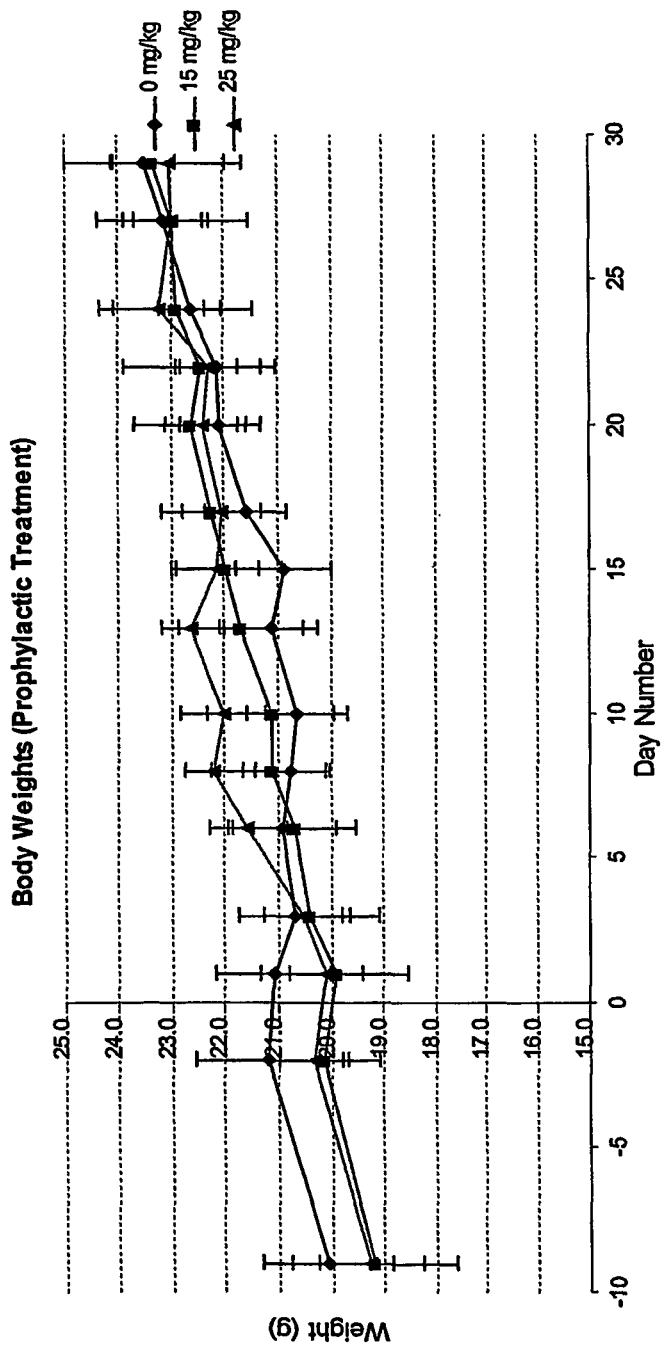

FIG. 33: Effect of prophylactic APFO administration on nu/nu mouse body weight.

Figure 34:
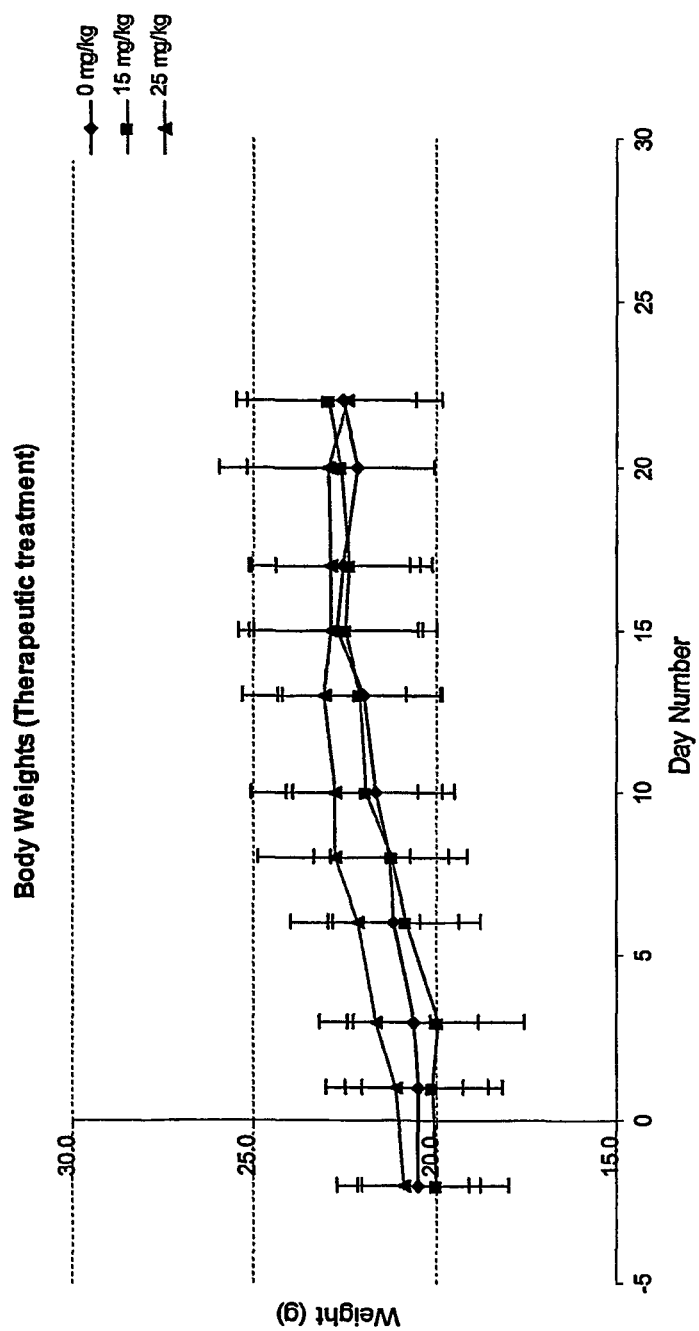

FIG. 34: Effect of therapeutic APFO administration on nu/nu mouse body weight.

Figure 35:
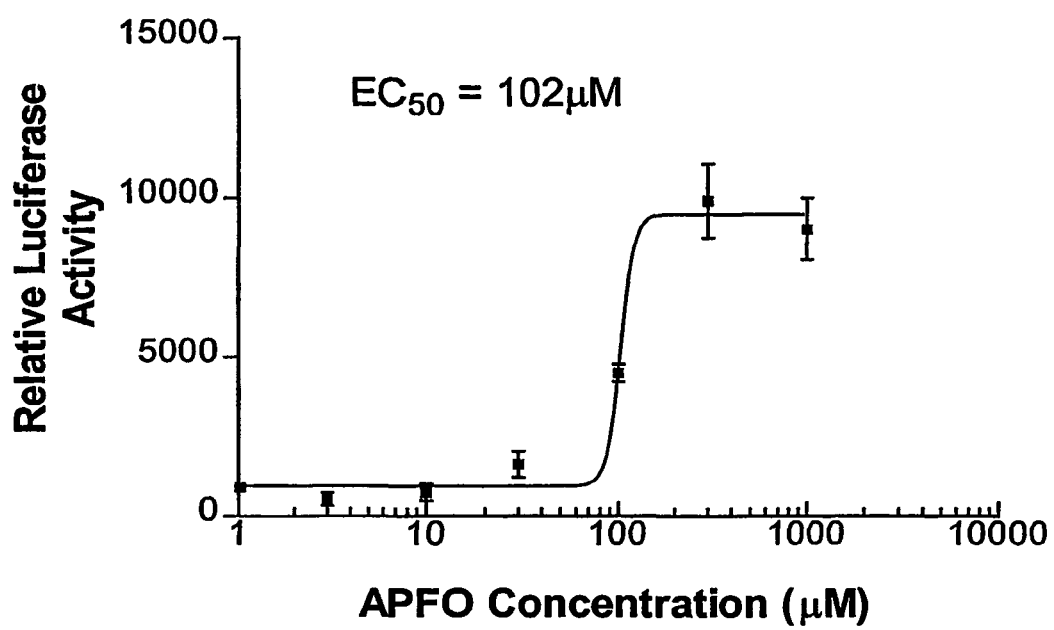

FIG. 35: Activation of Mouse PPARα by APFO.

Figure 36:
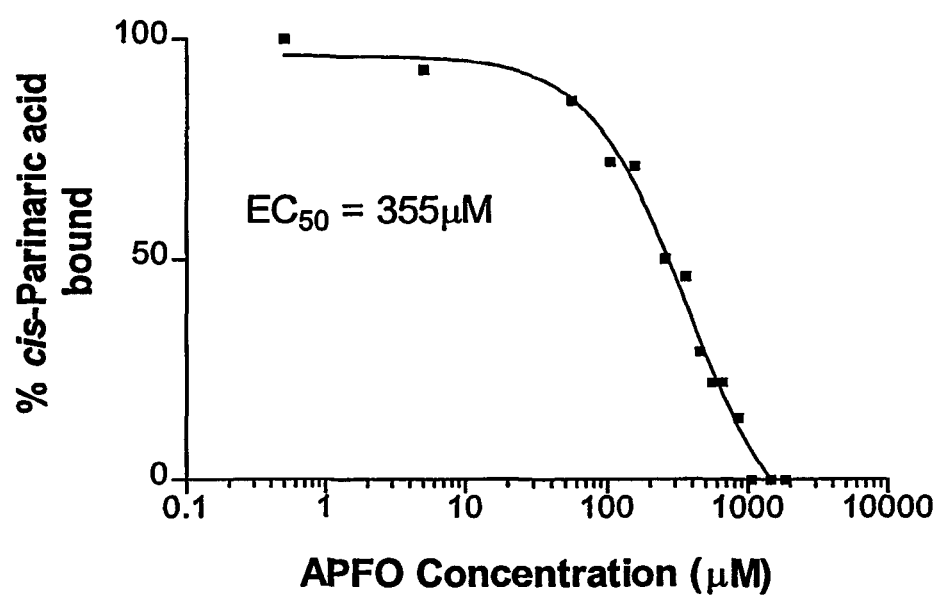

FIG. 36: Interaction of APFO with Ligand Binding Domain of Human PPARγ.

EXAMPLE 1

Effect of Perfluorinated Fatty Acid on Insulin, Glucose, Cholesterol and Triglyceride Levels, and on Body Weight Methods Male Fisher 344 rats (initially 6 weeks old) were administered ammonium perfluorooctanoate (APFO, 300 ppm) in the diet for periods of time up to one year. Control rats received powdered diet that did not contain APFO.

Body weights were initially determined daily and then weekly. Food consumption was determined weekly. Clinical observations were made daily.

Rats were sacrificed at 1, 2, 7, 14, 28, 90, 182 and 365 days. There were 8 rats per group. At sacrifice blood was sampled by cardiac puncture and submitted for clinical chemistry.

The following assay methods/kits were used:

| Assay | Supplier | Kit Number |
| --- | --- | --- |
| ALT | Roche Diagnostics | MPR 1087 568 |
| AST | Roche Diagnostics | Unimate 3 0736414 |
| Glucose | Roche Diagnostics | MPR2 1442 449 |
| Trigylcerides | Roche Diagnostics | Peridochrom GPO-PAP 701 882 |
| Cholesterol | Roche Diagnostics | CHOD-AP MPR3 236691 |
| Insulin | Amersham | RNP 2567 |

Results

Administration of APFO to male Fischer 344 rats lead to marked reductions in bodyweight gain (FIG. 1). Treated animals had body weights approximately 25-30% lower than concurrent controls. This weight change was not accompanied by any adverse clinical symptoms or changes in activity.

Food consumption expressed per rat was markedly decreased (to approximately 50% of control consumption) during the first week of treatment. However after this time food consumption per rat increased to 80-90% of control values (FIG. 2).

When expressed as weight of food consumed per unit bodyweight, food consumption was decreased by approximately 30% during the first week of APFO administration. However, at later times APFO-treated animals consumed between 10 and 30% more food per unit bodyweight than controls (FIG. 3).

Plasma cholesterol, glucose and insulin concentrations were decreased at all time points examined (FIGS. 4-6), while plasma triglycerides were decreased at 7 days and beyond (FIG. 7).

These data suggest that APFO and related compounds may be useful for treatment of obesity, diabetes, hypertriglycerideaemia and hypercholesterolaemia and diseases where alterations in lipid or eicosanoid status may be desirable, such as arthritis or cancer.

EXAMPLE 2

Effect of APFO in Reversing Obesity and Diabetes

The effect of APFO in animal models of obesity and diabetes was studied in order to establish the therapeutic potential of APFO to reverse obesity and diabetes.

The studies reported in Example 1 involving the administration of APFO to Sprague Dawley rats for up to one year, demonstrated the compound's anti-diabetic and anti-obesity potential. Following an initial reduction in food consumption during the first week of the study, an increase in food consumption per unit body weight was coupled to a marked reduction in body weight gain in treated animals throughout the test period. Furthermore, plasma cholesterol and insulin concentrations were decreased at all time points examined, while plasma glucose and triglycerides were decreased at 7 days and beyond.

In this Example, these observations in healthy rats are extended by investigations in two models of metabolic disease—the obese mouse (ob/ob) and the diabetic GK/Mol rat.

1.1 Mouse Model (ob/ob)

The C57BL/6J-ob/ob mouse is an obese, leptin-deficient animal that is widely accepted as a model of obesity and diabetes. Age-paired, disease-free (lean) animals (C57BL/6J-+/+) were also included in the study to observe the 'normal' response.

1.1.1 Experimental Design and Methods

Three groups (n=5) of ob/ob (C57BL/6J-ob/ob) mice were treated with 3 dose levels of APFO (5, 15 and 25 mg/kg/day). Animals were administered APFO, dissolved in water, by oral gavage, daily for 14 days. One group of 10 ob/ob mice was also treated with vehicle (water) alone. Additionally, to observe the 'normal' response, 5 age-paired, disease-free animals (C57BL/6J-+/+) were administered 25 mg/kg APFO and a similar disease-free control group was administered vehicle only.

Twenty-four hours after the last dose the animals were killed by an increasing concentration of carbon dioxide. Blood was collected by cardiac puncture and plasma prepared and stored at −70° C. until analysed. Major tissues were weighed, sampled, flash frozen in liquid nitrogen and stored at −70° C.

Plasma was analysed for triglycerides, cholesterol and glucose using kits purchased from Sigma (Poole, Dorset). Concentrations of plasma insulin and leptin were determined using commercially available enzymeimmunoassay-based kits from Amersham Life Sciences and Crystalchem Inc., (Chicago) respectively. All assays were carried out as specified by the manufacturer.

1.1.2 Results and Discussion

Both strains of mice treated at 25 mg/kg/day lost bodyweight over the treatment period. In +/+ mice this was only apparent after day 4; these animals also lost less weight, as a percentage of initial bodyweight, than the ob/ob mice (26% versus 33%). In ob/ob mice treated at 15 mg/kg/day 20% bodyweight loss was noted over the study period. Animals treated at 5 mg/kg/day were unaffected (FIG. 9). No other adverse clinical observations were observed.

The bodyweight losses were reflected in marked, APFO dose-related, decreases in food consumption (76%, 53% and 17% lower than control mice at the high, intermediate and low dose levels respectively) (FIG. 10). In +/+ mice a decrease in food consumption was evident over the first nine days of treatment, following which there was a steep recovery towards control values without equaling them. The overall consumption was still 31% lower than in +/+ controls. When expressed in terms of food consumed per gram of bodyweight the pattern of effect was similar, although the recovery in values seen in +/+ mice after day 9 was greater and the subsequent values more nearly equal to those of their controls (FIG. 11).

There was a very marked reduction (greater than 90%) in plasma insulin concentrations in all treated ob/ob mice, which was broadly related to dose level (FIG. 12). In +/+ mice, control insulin levels were notably lower than in the ob/ob mice. However, APFO-treatment still led to a marked reduction in plasma insulin concentrations.

APFO-treated (15 or 25 mg/kg/day) ob/ob mice showed dose-related reductions in plasma glucose down to approximately 20% of control values, similarly plasma triglyceride concentrations were decreased to 40% of control values (FIGS. 13 and 14). At 5 mg/kg/day administered to ob/ob mice, glucose was reduced by approximately 50% but there was no effect on triglyceride concentrations (FIG. 14). In +/+ mice, APFO (25 mg/kg/day) decreased glucose and triglycerides to 55% and 35% of control plasma values respectively.

At a dose of APFO of 25 mg/kg/day to both strains there was an approximate 30% reduction in plasma cholesterol concentrations. This was not evident at the low and mid dose levels in the ob/ob mice (FIG. 15).

Plasma leptin concentrations in the ob/ob mice were below the levels of quantitation; this was expected as there is an early stop codon within the leptin gene of this mouse strain. Treatment of the +/+ mouse, which possesses a normal leptin gene, with APFO (25 mg/kg/day) resulted in decreased plasma leptin concentrations to, or below the level of quantitation (FIG. 16).

Epididymal fat pad (white adipose tissue) weights were 7-fold higher in control ob/ob mice compared to control +/+ mice. APFO-treatment decreased the weight of the epididymal fat pads in a dose-related manner in ob/ob mice and +/+ mice (FIG. 17).

1.1.3 Conclusions

In summary, there were a number of significant physiological effects that could be related to the administration of APFO. In lean controls, there was a slight reduction in body weight, and this loss reached a nadir after 10 days with no weight loss occurring after this time. Food consumption in this group remained constant.

At the high and intermediate dose levels, ob/ob mice continued to lose body weight. At 25 mg/kg, ob/ob mice also displayed appetite loss (reflected in body weight changes). In this group there was also marked reduction in glucose levels. This appeared to suggest that the anti-obesity effects may have been due to reduced food consumption. However, in animals treated with 5 mg/kg APFO, a 17% reduction in food consumption was associated with a 50% reduction in plasma glucose levels, which suggested that the anti-obesity effects observed in ob/ob mice were due to metabolic changes caused by APFO, and not to a loss of appetite.

These data suggest that APFO causes weight loss in obese animals, but not, significantly, in lean animals and so may be used as an anti-obesity agent. Additionally the APFO-induced decreases in plasma glucose and insulin suggest that this chemical may be of therapeutic use in Type II diabetes.

1.2 Rat GK/Mol Model

The GK/Mol rat is a non-obese, diabetic animal that is widely accepted as a model of Type II diabetes. In order to measure the 'normal' response, non-diabetic Wistar rats were also used in the study.

1.2.1 Experimental Design and Methods

Three groups (n=5) of GK/Mol rats were administered 3 dose levels of APFO (3, 10 and 30 mg/kg). Animals were administered APFO by oral gavage, daily for 14 days. One group of 10 GK/Mol rats was also treated with vehicle (water) alone. Additionally, to observe the 'normal' response, 5 age-paired, disease-free Wistar rats were administered 30 mg/kg APFO and a similar disease-free group was administered vehicle only.

Twenty-four hours after the last dose the animals were killed by an increasing concentration of carbon dioxide. Blood was collected by cardiac puncture and plasma prepared and stored at $-70°$ C. until analysed. Major tissues were weighed, sampled, flash frozen in liquid nitrogen and stored at $-70°$ C.

Plasma was analysed for, triglycerides, cholesterol, glucose, insulin and leptin as described in section 1.1.1.

1.2.2 Results and Discussion

APFO administration to GK/Mol rats resulted in a dose-dependent decrease in body weight gain to 90%, 71% and 44% of control values at the low, mid and high dose levels respectively (FIG. 18). There was no effect on bodyweight gain in treated Wistar rats.

Treated GK/Mol rats had slightly lower total food consumption (86-98% of control values), although this difference was not related to dose level (FIG. 19). There was no difference in food consumption between treated Wistar rats and their controls. No pattern was discernible when the data were expressed as food eaten per gram of bodyweight (FIG. 20).

There was a marked dose-dependent reduction in the plasma concentration of insulin, reaching about 10% of control values in both strains of rat (FIG. 21).

Plasma glucose concentrations in GK/Mol rats were lowered by APFO to about 85% of control values at dose levels of 30 mg/kg/day (FIG. 22). Plasma Triglycerides (FIG. 23) and cholesterol (FIG. 24) concentrations were lower by between 10 and 20% in treated GK/Mol rats. In Wistar rats, plasma cholesterol was reduced to 73% of control values.

Group mean plasma concentrations of leptin (FIG. 25) were slightly lower (by approximately 40%) in Wistar rats treated at 30 mg/kg/day than in their controls. There were no differences in leptin concentrations in the GK/Mol rats that could be indicative of a treatment-related effect.

1.2.3 Conclusions

The GK/mol study followed a similar pattern to the investigation in Sprague Dawley rats (Example 1). APFO caused a reduction in the levels of glucose, triglycerides and cholesterol coupled to reduced weight gain in treated animals; there was also a marked reduction in the level of plasma insulin.

In conclusion APFO demonstrated anti-diabetic effects in a rat model for type II diabetes, further indicating it may be an effective agent for the treatment of this condition.

2. Therapeutic Potential of APFO as an Anti-cancer Agent

The effect of APFO in vitro against human tumour cell lines and in vivo in a human tumour xenograft model was examined.

2.1 In Vitro Anti-Tumour Activity

Three human cancer cell lines were exposed to APFO and cytotoxicity levels assessed in order to assess APFO's functions as an anti-cancer agent.

2.1.1 Experimental Design and Methods

HT-29 cells (human colon tumour-derived), MCF7 cells (human breast cancer-derived) and HepG2 cells (human liver cancer-derived) were cultured in Dulbecco's Modified Eagles Medium (DMEM) supplemented with 10% heat-inactivated foetal calf serum, 2 mM L-glutamine, penicillin (50 IU/ml), streptomycin (50 µg/ml) and 1% non-essential amino acids. Cells were harvested by trypsinisation and diluted to $5 \times 10^4$ cells/ml, and 200 µl of cell suspension was plated into each well of a 96 well plate and allowed to attach overnight at 37° C. with 5% $CO_2$. Cells were exposed to various concentrations of APFO in growth medium (0.01, 0.03, 0.1, 0.3, 1, 3, 10, 30 and 100 and 1000 µM) for four hours. 20 µl of a 5 mg/1 m MTT solution was added to each well and the cells were incubated for 4 hours at 37° C. The medium was removed and 200 µl DMSO was added to dissolve formazan crystals. Plates were read at 570 nm and background at 690 nm was subtracted. Results were displayed graphically as percentage cell survival versus APFO concentration.

2.1.2 Results and Discussion

APFO elicited a cytotoxic effect after 4 hours at concentrations exceeding 500 µM (FIG. 26).

2.1.3 Conclusions

This study indicated that APFO was effective at killing a range of human cancers in vitro.

2.2 HT-29 Xenograft Model in Nude Mice

The objective of this study was to examine the anti-tumour capabilities of APFO in a xenografted animal model. Effects of APFO on tumour progression were tested on a human colon cancer-derived cell line xenografted into immune-deficient nu/nu mice. Prophylactic and therapeutic effects of APFO were assessed by measurement of tumour size at regular intervals during administration of APFO.

2.2.1 Experimental Design and Methods

Athymic nude (nu/nu) mice from ICRF stock (HsdOla:ICRF-nu) were obtained from Clare Hall (Pofters Bar, UK). All animals were female and approximately 9 weeks old. Animals, housed in isolator cages and handled under laminar flow, were divided into one control group and two treatment groups, with 5 female mice per group for both the prophylactic and therapeutic schedules HT-29 cells were cultured according to the conditions described in section 2.1.1. Cells were harvested, pooled by centrifugation and resuspended in 5 ml medium to which 5 ml Matrigel (basement membrane matrix) was added. 100 µl of cell suspension was injected subcutaneously into each flank of the mice ($1.75 \times 10^6$ cells per flank). In order to assess the prophylactic effect of APFO, half of the animals were administered the compound immediately following tumour cell implantation. For the therapeutic schedule, APFO was injected once tumours had developed.

Animals were administered APFO, dissolved in water, by intra-peritoneal (ip) injection 3 times per week for one month. The doses of APFO were 15 mg/kg and 25 mg/kg bodyweight. The volume of the dosing solution was 10 ml/kg bodyweight. Control animals received an equivalent volume of water.

Animal bodyweights were recorded throughout the study. Tumour growth was measured 3 times per week using digital calipers and the volume was calculated using the formula:

$$4/3\pi \cdot \left\{ \frac{(d_1 + d_2)^3}{4} \right\}$$

Where $d_1$=mean length (n=2) and $d_2$=mean width (n=2). (NB, n=4 if tumour was an irregular shape).

The maximum permitted tumour volume, according to the terms of the Home Office license, was 1.44 cm$^3$. Results were expressed graphically for each time point as mean tumour volumes. Tumour weights were recorded at the end of the study, and tumour samples were either snap frozen in liquid nitrogen or fixed in formal saline for further analysis.

2.2.2 Results and Discussion

HT-29-derived tumours developed approximately 14 days into the study.

Tumour growth in both prophylactic and therapeutic groups proceeded at a much faster rate in control groups compared to tumours in APFO-treated animals (FIGS. 27 and 30 respectively). Consequently, the therapeutic study was not completed because control animals were lost either because tumour volume exceeded the permitted size, or because the tumours were deemed ulcerated and again continuance was not permitted under the terms of the Project License. Hence, animals in the therapeutic study were injected at 8 time points compared to 13 time points in the prophylactic study.

Tumour growth rate in animals treated prophylactically was markedly slower in APFO-treated animals, with a lag phase of 15 days for control groups compared to 22 days for APFO-treated mice (FIG. 27). In animals administered 25 mg/kg APFO, tumour growth reached a plateau after 26 days, while in animals dosed at 15 mg/kg, tumour volume continued to increase (FIG. 27). Tumour volume in the prophylactic groups increased 18 fold in controls, 8 fold at 15 mg/kg and 6 fold at 25 mg/kg between the start of tumour measurement (day 1) and the end of the study (day 15) (FIG. 28). Upon necroscopy, in the 15 mg/kg and 25 mg/kg groups respectively, tumour weights were 22% and 58% smaller than in control animals (FIG. 29).

Tumour growth rate was also markedly slower in animals treated therapeutically with APFO, with a lag phase of 17 days in control tumours compared to 26 days in treated mice (FIG. 30). No plateau was reached in the highest dose group, but the study was incomplete as animals were treated for a shorter period than intended. Tumour volume increased 15-fold in controls, 14-fold at 15 mg/kg, and 7-fold at 25 mg/kg between day 1 and day 17 (FIG. 31). Tumour weights were 45% and 37% smaller in the 15 mg/kg and 25 mg/kg dose groups respectively (FIG. 32). It should be noted that 5 animals (4 controls and 1 high dose animal) had been lost from the study, thus affecting mean values of final tumour weights.

Tumours were removed from animals at the end of the study period and examined macroscopically. Control tumours from the prophylactic group were solid, while APFO-treated animals produced tumours that were fluid-filled, suggesting cell death in the centre of the tumours. Differences between control and treated groups were less obvious in animals treated therapeutically, but these animals were dosed for a shorter period. Samples of tumours were formalin fixed and also flash frozen in liquid nitrogen for histopathological examination.

Animal body weights were monitored and recorded throughout the study. There was no significant difference between control and treated animals in either the prophylactic or therapeutic groups in animals implanted with HT-29 cells (FIGS. 33 and 34).

2.2.3 Conclusions

In summary, APFO demonstrated anti-tumour capabilities in a human cancer cell line when either given concomitantly with the tumour cells or following tumour establishment. Additionally, body weight remained unaffected by the test agent, suggesting that treatment-associated weight loss would not occur, a major advantage for chemotherapeutic agent. It is probable that treatment-associated weight loss did not occur because APFO selectively targets obese subjects and not lean subjects (eg. nu/nu mice).

Finally, APFO showed anti-tumour capabilities against HT-29 cells, a human colon cancer cell line, thus demonstrating that it is capable of inhibiting the growth of human tumour cells.

3. The Potential Anti-Inflammatory Properties of APFO

3.1 In vitro Studies

The ability of APFO (or other test compound) to inhibit cyclooxygenase 1 (COX1) and cyclooxygenase 2 (COX-2) inhibition is examined using an EIA-based human COX inhibitor assay kit as described by the manufacturer (Cayman Chemical, Michigan).

3.2 In Vivo Studies

The anti-inflammatory potential of APFO (or other test compound) is examined in a rat model. Animals are dosed with APFO or dexamethasone, after which the animal's immune system is challenged with lipopolysaccharide (LPS) and plasma cytokines are measured. The study may consist of one control group and three treatment groups, with 10 male CD rats (80-120 g) per group. The control group is administered vehicle (water) only followed by LPS (30 µg per 100 g rat) 24 hrs later. Treatment group 1 animals receive APFO (or other test compound) at 30 mg·kg. Treatment group 2 animals receive APFO (or other test compound) at 30 mg·kg followed by LPS (30 µg per 100 g rat) 24 hrs later. Treatment group 3 animals received dexamethasone (10 mg·ml in corn oil) followed by LPS (30 µg per 10 g rat) 1 hour later. The plasma from 5 animals per group is harvested 1 hour or 2 hours post-treatment. Plasma cytokines (II-6, II-1β and TNF) are measured using commercially available kits as specified by the manufacturer (Endogen Inc., Massachusetts).

4. Interaction of APFO with PPAR Isoforms

Transactivation assays involving mouse PPAR alpha cDNA and ligand binding assays using human PPAR gamma were performed in order to demonstrate that APFO interacts with PPAR isoforms.

4.1 Mouse PPAR Transactivation Assay

4.1.1 Experimental Design and Methods

COS-1 cells (cultured in medium described in section 2.1.1 but without non-essential amino acids) were plated into 6 well tissue culture dishes at $3\times10^5$ cells per well and allowed to adhere overnight at 37° C. The next day the medium was aspirated and the cells washed with PBS, pH7.4, and 200 µl of a transient transfection cocktail was added to each well. The transfection cocktail was composed of 50 ng of vector DNA carrying mouse PPAR alpha, 500 ng of plasmid DNA containing the PPAR response element of liver fatty acid binding protein and, as a transfection control, 500 ng of a vector harbouring β-Galactosidase. DNA was dissolved in PBS containing 50 µg·ml DEAE-Dextran. Control cells were exposed to a transfection cocktail that contained no plasmid DNA. Cells were incubated at 37° C. for 30 minutes before 2 ml of medium containing 80 µM chloroquine was added and the cells incubated for a further 2.5 hours at 37° C. The medium was aspirated and the cells shocked with 10% DMSO in medium for 2.5 minutes at room temperature. Cells were washed with PBS then allowed to recover at 37° C. in growth medium for 24 hours.

Transiently transfected cells were exposed to APFO (dissolved in water) in medium at 0, 3, 10, 30, 100, 300 and 1000 µM for 16 hours at 37° C. Cells were then washed, lysed, and luciferase and β-Galactosidase activities were measured using kits according to the methods specified by the manufacturer (Promega, Madison, USA) by flash luminescence and spectophotometry respectively. Luciferase expression was normalised by dividing by the flash luminescence reading with constitutive β-Galactosidase expression levels measured at 415 nm following a colourimetric assay.

Data were graphed, fitted to non-linear regression curves and $EC_{50}$ values calculated using GraphPad Prism software.

4.1.2 Results and Discussion

Activation of mouse PPAR alpha by APFO occurred, with an effective concentration ($EC_{50}$) of 102 µM. (FIG. 27).

4.1.3 Conclusions

The data presented here demonstrate that APFO is a mouse PPAR alpha activator at µM concentrations.

4.2 PPAR Gamma Ligand Binding Studies

His-tagged human PPARγ ligand binding domain was expressed in *E. Coli* as described previously [Palmer, CAN and Wolf, C R. FEBS Letts. 431, 476-480, (1998)]. The receptor protein was partially purified by nickel affinity chromatography.

4.2.1 Ligand Binding Studies

This recombinant receptor protein has been used previously to study interactions with the fluorescent fatty acid—cis-parinaric acid (CPA)[Palmer CAN and Wolf C R. FEBS Letts. 431, 476-480, (1998); Causevic M, Wolf C R and Palmer CAN. FEBS Letts. 463, 205-210, (1999)]. On binding to the receptor, changes in the spectral properties of the fatty acid occurs. These are quantitatively related to the binding of the ligand to the receptor and can be used to calculate binding constants. A competitive displacement assay can be utilised to examine the binding characteristics of other compounds. APFO was assayed for its ability to displace cis-parinaric acid from PPARγ by this method. Data were analysed as described in section 4.1.

4.2.2 Results and Discussion

Competitive ligand binding assays using the ligand binding domain of human PPAR gamma showed that displacement of cis-parinaric acid occurred, with an $EC_{50}$ of 355 µM (FIG. 28).

3.2.4 Conclusions

These data indicate that APFO interacts with the ligand binding domain of human PPAR gamma.

The invention claimed is:

1. A method of treatment of cancer in a human patient, comprising:
    administering to the patient an effective amount of a compound of perfluorooctanoic acid or a pharmaceutically salt thereof.

2. The method of claim 1 wherein the compound is ammonium perfluorooctanoate.

3. A method of treatment of breast, liver, or colon cancer in a human patient, comprising:
    administering to the patient an effective amount of a compound of perfluorooctanoic acid or a pharmaceutically acceptable salt thereof.

4. The method of claim 3 wherein the compound is ammonium perfluorooctanoate.

* * * * *

UNITED STATES PATENT AND TRADEMARK OFFICE
CERTIFICATE OF CORRECTION

PATENT NO. : 8,487,003 B2
APPLICATION NO. : 10/468331
DATED : July 16, 2013
INVENTOR(S) : Elcombe et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1688 days.

Signed and Sealed this
Eighth Day of September, 2015

Michelle K. Lee
*Director of the United States Patent and Trademark Office*